United States Patent
Wood et al.

(10) Patent No.: US 10,786,314 B2
(45) Date of Patent: Sep. 29, 2020

(54) SURGICAL IMAGING APPARATUS AND METHODS

(71) Applicant: SYNAPTIVE MEDICAL (BARBADOS) INC., Bridgetown (BB)

(72) Inventors: Michael Wood, Toronto (CA); Cameron Piron, Toronto (CA); Murugathas Yuwaraj, Markham (CA); Gal Sela, Toronto (CA); Joshua Richmond, Toronto (CA); Stephen McFadyen, Toronto (CA)

(73) Assignee: Synaptic Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 16/414,957

(22) Filed: May 17, 2019

(65) Prior Publication Data

US 2020/0015908 A1  Jan. 16, 2020

Related U.S. Application Data

(63) Continuation of application No. 14/398,649, filed as application No. PCT/CA2014/050268 on Mar. 14, 2014, now Pat. No. 10,292,771.

(Continued)

(51) Int. Cl.
*A61B 34/20* (2016.01)
*G01J 3/28* (2006.01)
(Continued)

(52) U.S. Cl.
CPC .............. *A61B 34/20* (2016.02); *A61B 1/042* (2013.01); *A61B 1/043* (2013.01); *A61B 1/0646* (2013.01);
(Continued)

(58) Field of Classification Search
CPC ... A61B 5/0084; A61B 5/0075; A61B 5/0071; A61B 1/00009; A61B 5/0059;
(Continued)

(56) References Cited

U.S. PATENT DOCUMENTS 7,616,303 B2 * 11/2009 Yang .................. A61B 5/14535
356/300
2009/0292168 A1 * 11/2009 Farr .................... A61B 1/00186
600/109

(Continued)

*Primary Examiner* — Farhan Mahmud
(74) *Attorney, Agent, or Firm* — Thanh Vuong

(57) ABSTRACT

A hyperspectral imaging apparatus and methods for performing hyperspectral imaging of a surgical field, involving: an external optical imaging device for externally imaging internal tissue through a surgical access port, the access port having a port wall having a light-diffusing surface texture, whereby reflectance of the port wall is decreasable, and the external optical imaging device having an illuminated exoscope, the illuminated exoscope having: a longitudinal housing; an optical imaging assembly provided within the longitudinal housing; an imaging camera interfaced with the optical imaging assembly for detecting images collected by the optical imaging assembly; and one or more illumination sources supported by the longitudinal housing, wherein an illumination axis associated with each illumination source is offset from an imaging axis of the optical imaging assembly; a remote light source; a spectral filtering device in optical communication with the remote light source; and a light guide having a proximal end in optical communication with an output of the spectral filtering device and one or more distal ends, wherein each distal end is in optical communication with an illumination source.

20 Claims, 18 Drawing Sheets

Related U.S. Application Data

(60) Provisional application No. 61/800,911, filed on Mar. 15, 2013, provisional application No. 61/800,695, filed on Mar. 15, 2013, provisional application No. 61/801,530, filed on Mar. 15, 2013, provisional application No. 61/818,223, filed on May 1, 2013, provisional application No. 61/818,280, filed on May 1, 2013.

(51) Int. Cl.
| | | |
|---|---|---|
| *G01J 3/42* | (2006.01) | |
| *G01J 3/02* | (2006.01) | |
| *A61B 5/00* | (2006.01) | |
| *A61B 1/04* | (2006.01) | |
| *A61B 1/06* | (2006.01) | |
| *A61B 90/00* | (2016.01) | |
| *A61B 34/10* | (2016.01) | |
| *A61B 1/313* | (2006.01) | |
| *A61B 5/02* | (2006.01) | |
| *A61B 6/03* | (2006.01) | |
| *A61B 6/00* | (2006.01) | |
| *A61B 17/00* | (2006.01) | |
| *A61B 90/50* | (2016.01) | |
| *A61B 34/30* | (2016.01) | |
| *A61B 90/30* | (2016.01) | |
| *A61B 5/055* | (2006.01) | |

(52) U.S. Cl.
CPC .......... *A61B 1/313* (2013.01); *A61B 5/02007* (2013.01); *A61B 5/4064* (2013.01); *A61B 6/032* (2013.01); *A61B 6/505* (2013.01); *A61B 17/00234* (2013.01); *A61B 34/10* (2016.02); *A61B 90/37* (2016.02); *G01J 3/0229* (2013.01); *G01J 3/2823* (2013.01); *G01J 3/42* (2013.01); *A61B 5/0066* (2013.01); *A61B 5/055* (2013.01); *A61B 5/4029* (2013.01); *A61B 5/4504* (2013.01); *A61B 5/4514* (2013.01); *A61B 5/4519* (2013.01); *A61B 5/4523* (2013.01); *A61B 5/4533* (2013.01); *A61B 5/4547* (2013.01); *A61B 5/4552* (2013.01); *A61B 5/7246* (2013.01); *A61B 5/7271* (2013.01); *A61B 34/30* (2016.02); *A61B 90/50* (2016.02); *A61B 2034/107* (2016.02); *A61B 2034/2051* (2016.02); *A61B 2034/2055* (2016.02); *A61B 2090/306* (2016.02); *A61B 2090/364* (2016.02); *A61B 2090/3616* (2016.02); *A61B 2090/3735* (2016.02); *A61B 2505/05* (2013.01); *A61B 2576/026* (2013.01)

(58) Field of Classification Search
CPC . A61B 19/5202; A61B 19/5212; A61B 1/043; A61B 1/0646; A61B 1/0653; A61B 1/07; A61B 19/5223; G01J 3/2823; G01J 3/10; G01J 3/0208
See application file for complete search history.

(56) References Cited

U.S. PATENT DOCUMENTS

| | | | | |
|---|---|---|---|---|
| 2010/0056928 | A1* | 3/2010 | Zuzak | A61B 5/0071 600/476 |
| 2011/0130627 | A1* | 6/2011 | McGrail | A61B 1/00016 600/109 |
| 2011/0270092 | A1* | 11/2011 | Kang | G01J 3/2823 600/476 |

* cited by examiner

SURGICAL IMAGING APPARATUS AND METHODS

CROSS-REFERENCE TO RELATED APPLICATION(S)

This continuation application claims priority to, and the benefit of, U.S. patent application Ser. No. 14/398,649, entitled "SURGICAL IMAGING SYSTEMS," filed on Nov. 14, 2014; U.S. Provisional Application No. 61/800,911, titled "HYPERSPECTRAL IMAGING DEVICE," filed on Mar. 15, 2013; U.S. Provisional Application No. 61/800,695, entitled "EXTERNAL VIDEO SCOPE FOR PORT-BASED SURGICAL PROCEDURES," filed on Mar. 15, 2013; U.S. Provisional Application No. 61/818,223, entitled "IMAGING ASSEMBLY FOR ACCESS PORT-BASED MEDICAL PROCEDURES," filed on May 1, 2013; U.S. Provisional Application No. 61/801,530, entitled "SYSTEMS, DEVICES AND METHODS FOR PLANNING, IMAGING, AND GUIDANCE OF MINIMALLY INVASIVE SURGICAL PROCEDURES," filed on Mar. 15, 2013; and U.S. Provisional Application No. 61/818,280, entitled "SYSTEMS, DEVICES AND METHODS FOR PLANNING, IMAGING, AND GUIDANCE OF MINIMALLY INVASIVE SURGICAL PROCEDURES," filed on May 1, 2013, all of which are hereby incorporated herein by reference in their entirety.

FIELD

The present disclosure relates to imaging methods for use in minimally invasive therapy and image guided medical procedures using optical imaging, and more particularly, hyperspectral imaging.

BACKGROUND

In the related art, the optical absorption and scattering properties of biological tissue depend on both the chemical and structural properties of the tissue and the wavelength of the interacting light. The manner in which these absorption and scattering properties of tissue change, as a function of light, is particularly useful, and is often unique to chemicals or structures in the tissue (the spectrum of the tissue). For example the absorption features of oxy-hemoglobin and deoxy-hemoglobin can be used to measure the oxygenation of blood and tissue, and the scatter changes caused by difference cellular sizes can be used to detect precancerous and cancerous tissue. The field of measuring these changes in optical properties, as a function of light, is known as spectroscopy; and the device to measure the light at the various wavelengths is known as a spectrometer. Spectroscopy has found a wealth of current and potential applications in medicine.

Traditional spectrometers measure the spectrum of light from a single point of a sample. However, the spectrum from multiple spatial points can be combined to form a three-dimensional (3D) spatial dataset (sometimes referred to as a hypercube), wherein the first two dimensions are spatial and the third is wavelength. In other words, each image pixel has an entire spectrum rather than just an intensity or RBG value. This is known as hyperspectral imaging and is a powerful technique as spatially resolved tissue chemical or microstructural properties can imaged, thus providing a more complete understanding of the tissue and is a useful technique for tissue differentiation. According to a paper by Dicker et al., "Differentiation of Normal Skin and Melanoma using High Resolution Hyperspectral Imaging," hyperspectral image analysis (or hyperspectral imaging) was applied to search for spectral differences between benign and malignant dermal tissue in routine hematoxylin eosin stained specimens, e.g., normal and abnormal skin, benign nevi and melanomas. The results revealed that all skin conditions in the initial data sets could be objectively differentiated providing that staining and section thickness was controlled.

SUMMARY

To address at least the challenges experienced in the related art, the present disclosure involves systems, apparatuses, devices, and methods for illuminating tissue with monochromatic or broadband light and imaging light that has been reflected back from the tissue. Imaging is white-light imaging or hyperspectral imaging. The system can be a stand-alone hyperspectral imaging system, integrated as part of an external video scope, or as an auxiliary imaging module on an external videoscope. Various elements of a video scope that is particularly suited for minimally invasive surgery is first presented and then its configurations suitable for hyperspectral imaging are explained.

Accordingly, in a first aspect, there is provided a hyperspectral imaging apparatus for performing hyperspectral imaging of a surgical field, the hyperspectral imaging apparatus comprising: an illuminated exoscope comprising: a longitudinal housing; an optical imaging assembly provided within said longitudinal housing; an imaging camera interfaced with said optical imaging assembly for detecting images collected by said optical imaging assembly; and one or more illumination sources supported by said longitudinal housing, wherein an illumination axis associated with each illumination source is offset from an imaging axis of said optical imaging assembly; a remote light source; a spectral filtering device in optical communication with said remote light source; and a light guide having a proximal end in optical communication with an output of said spectral filtering device and one or more distal ends, where each distal end is in optical communication with an illumination source.

In another aspect, there is provided a method of performing hyperspectral imaging while providing a white light video feed, the method comprising: providing a hyperspectral apparatus as described above, wherein said imaging camera has a frame rate in excess of a pre-selected video frame rate; while obtaining hyperspectral image data; intermittently acquiring white light image frames at an acquisition rate equal to the pre-selected video frame rate; and rendering a white light video feed based on the acquired white light image frames.

In another aspect, there is provided an exoscope for imaging a surgical field within an access port during a medical procedure, the exoscope comprising: a longitudinal housing; an optical imaging assembly provided within said longitudinal housing, said optical imaging assembly comprising a working distance greater than approximately 25 cm; an imaging zoom camera interfaced with said optical imaging assembly for detecting images collected by said optical imaging assembly; wherein said optical imaging assembly and said imaging zoom camera are configured such that a minimum field of view associated with images collected by said imaging zoom camera is approximately equal to the diameter of the access port.

In accordance with an embodiment of the present disclosure, a hyperspectral imaging apparatus for performing hyperspectral imaging of a surgical field, the apparatus comprises: an external optical imaging device for externally imaging internal tissue through a surgical access port, the access port comprising a port wall having a light-diffusing surface texture, whereby reflectance of the port wall is decreasable, and the external optical imaging device comprising an illuminated exoscope, the illuminated exoscope comprising: a longitudinal housing; an optical imaging assembly provided within the longitudinal housing; an imaging camera interfaced with the optical imaging assembly for detecting images collected by the optical imaging assembly; and one or more illumination sources supported by the longitudinal housing, wherein an illumination axis associated with each illumination source is offset from an imaging axis of the optical imaging assembly; a remote light source; a spectral filtering device in optical communication with the remote light source; and a light guide having a proximal end in optical communication with an output of the spectral filtering device and one or more distal ends, wherein each distal end is in optical communication with an illumination source.

In accordance with an embodiment of the present disclosure, a method of fabricating a hyperspectral imaging apparatus for performing hyperspectral imaging of a surgical field, the method comprises: providing an external optical imaging device for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising: providing a longitudinal housing; providing an optical imaging assembly provided within the longitudinal housing; providing an imaging camera interfaced with the optical imaging assembly for detecting images collected by the optical imaging assembly; and providing one or more illumination sources supported by the longitudinal housing, wherein an illumination axis associated with each illumination source is offset from an imaging axis of the optical imaging assembly; providing a remote light source; providing a spectral filtering device in optical communication with the remote light source; and providing a light guide having a proximal end in optical communication with an output of the spectral filtering device and one or more distal ends, wherein each distal end is in optical communication with an illumination source In accordance with an embodiment of the present disclosure, a method of performing hyperspectral imaging of a surgical field by way of a hyperspectral imaging apparatus, the method comprises: providing a hyperspectral imaging apparatus, providing the apparatus comprising: providing an external optical imaging device for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising: providing a longitudinal housing; providing an optical imaging assembly provided within the longitudinal housing; providing an imaging camera interfaced with the optical imaging assembly for detecting images collected by the optical imaging assembly; and providing one or more illumination sources supported by the longitudinal housing, wherein an illumination axis associated with each illumination source is offset from an imaging axis of the optical imaging assembly; providing a remote light source; providing a spectral filtering device in optical communication with the remote light source; and providing a light guide having a proximal end in optical communication with an output of the spectral filtering device and one or more distal ends, wherein each distal end is in optical communication with an illumination source; and operating the apparatus.

A further understanding of the functional and advantageous aspects of the disclosure can be realized by reference to the following detailed description and drawings.

BRIEF DESCRIPTION OF THE DRAWING(S)

Embodiments will now be described, by way of example only, with reference to the drawings, in which.

DETAILED DESCRIPTION

Figure 1:
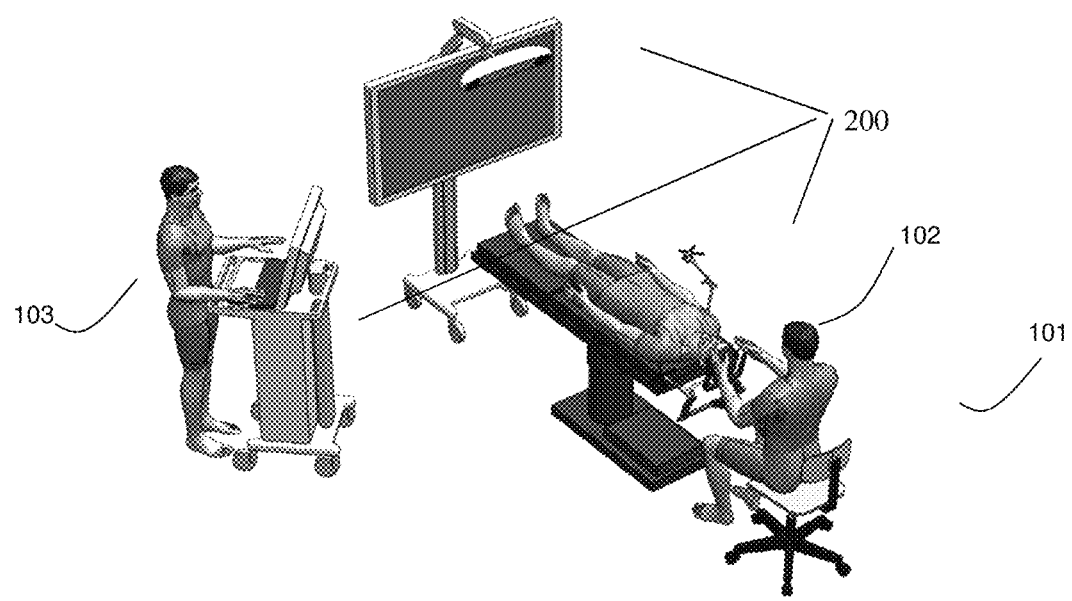
FIG. 1 is a diagram illustrating a navigation system which supports minimally invasive access port-based surgery, in accordance with an embodiment of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Port-based surgery is a minimally invasive surgical technique where a port is introduced to access the surgical region of interest using surgical tools. Unlike other minimally invasive techniques, such as laparoscopic techniques, the port diameter is larger than tool diameter. Hence, the tissue region of interest is visible through the port. Accordingly, exposed tissue in a region of interest at a depth few centimeters below the skin surface, and accessible through a narrow corridor in the port, is visualized using externally positioned optical systems such as microscopes and video scopes.

Current methods of tissue differentiation during port-based surgical procedure involves visual verification using externally placed video scope. Tissue differentiation is useful because surgeons do not have a quantitative means of effectively confirming tissues types during a surgical procedure. Traditionally, hyperspectral imaging has not been anticipated for intra-operative use in brain surgery because this method has a very limited depth of penetration in tissue and may not be effectively used transcranially.

Further, the narrow corridor in port-based surgery is often occluded when a vessel is accidentally cut. In these incidents, the surgeon is required to stop his current surgical process, e.g., opening of dura, slight retraction of the sulcus for trans-sulcus navigation of port or resection of tumor tissue, and irrigate the cavity to get a better view of the cavity. Further, such bleeding also limits the surgeon from quickly identifying the location of bleeding so that the particular vessel wall can be coagulated to terminate bleeding.

Accordingly, in some aspects of the present disclosure, systems and methods are provided for utilizing optical imaging in minimally invasive port based surgical procedures. In some embodiments, hyperspectral devices and methods are described for performing intraoperative tissue differentiation and analysis during such procedures.

Referring to FIG. 1, this diagram illustrates an example navigation system to support minimally invasive access port-based surgery, in accordance with an embodiment of the present disclosure. A surgeon 101 conducts a minimally invasive port-based surgery on a patient 102 in an operating room (OR) environment. A navigation system 200 comprising an equipment tower, cameras, displays, and tracked instruments assist the surgeon 101 during his procedure. An operator 103 is also present to operate, control, and provide assistance for the navigation system 200.

Figure 2:
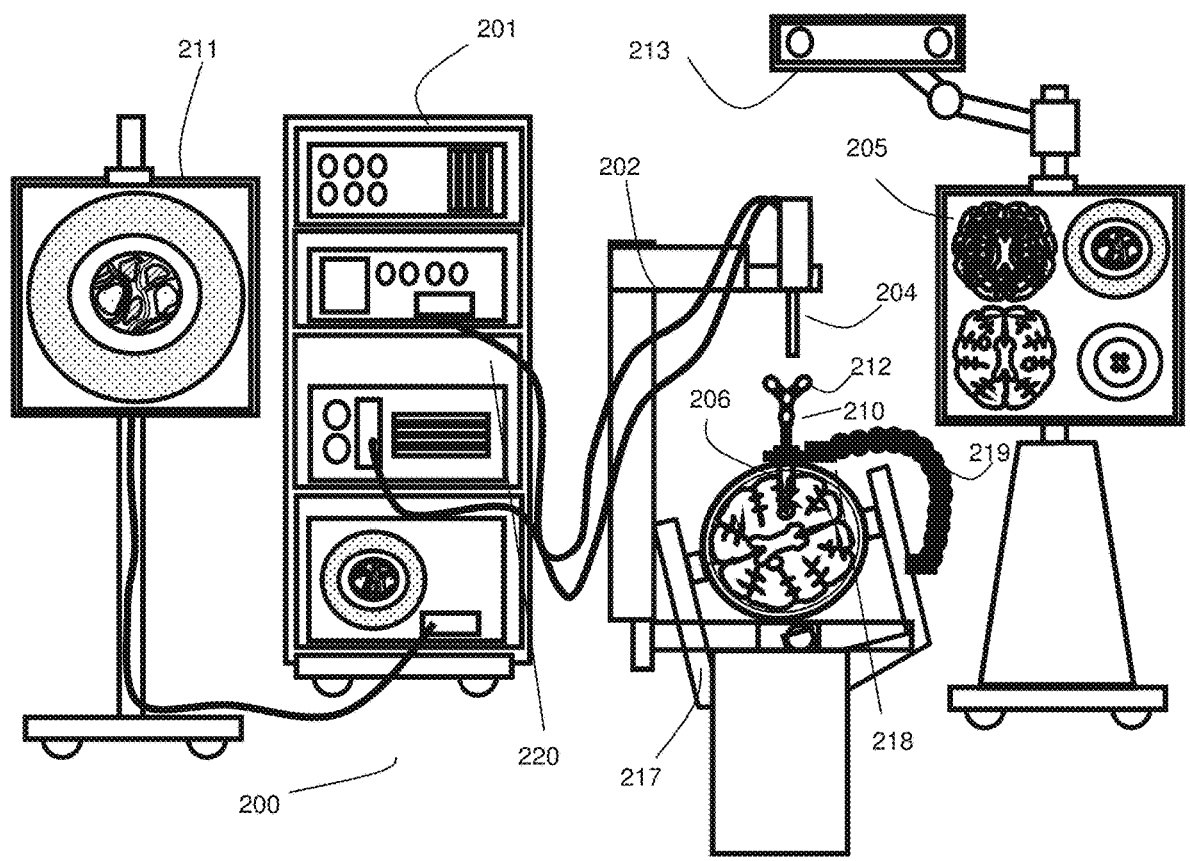
FIG. 2 is a block diagram illustrating system components of a navigation system, in accordance with an embodiment of the present disclosure.

Referring to FIG. 2, this block diagram illustrates system components of an example navigation system, in accordance with an embodiment of the present disclosure. The navigation system 200 comprises: a monitor 211 for displaying a video image, an equipment tower 201, a mechanical arm 202, which supports an optical scope 204. An equipment tower 201 is mounted on a frame, e.g., a rack or cart, and comprises at least one of: a computer, planning software, navigation software, a power supply, and software to manage the automated arm and tracked instruments. This example embodiment encompasses the equipment tower 201 as a single tower configuration with dual displays 211, 205; however, other configurations are also implementable, e.g., dual tower, single display, etc. Further, the equipment tower 201 is also configured with a UPS (universal power supply) to provide for emergency power, in addition to a regular AC adapter power supply.

Still referring to FIG. 2, the present disclosure also encompasses the equipment tower 201 having a recording module 220 that provides real-time recording of the surgical procedure, such as capturing audio data, video data, sensory data, and multi-modal imaging data or input, e.g., via computerized tomography (CT), magnetic resonance (MR), ultrasound (US), etc., from different sources. All relevant data is received at equipment tower 201 and stored in memory by recording module 220. The surgical procedure is automatically recorded at the outset or be controlled by the operator and/or administrator. In other embodiments, the procedure is automatically recorded (by default), but there is an option to override or delete the recording after the procedure has been completed.

Still referring to FIG. 2, the patient's brain is held in place by a head holder 217 and inserted into the head is an access port 206 and introducer 210. The introducer 210 is tracked using a tracking system 213, which provides position information for the navigation system 200. Tracking system 213 is a 3D optical tracking stereo camera similar to one made by Northern Digital Imaging (NDI). Location data of the mechanical arm 202 and port 206 is determined by the tracking system 213 by detection of fiducial markers 212 placed on these tools. A secondary display 205 may provide output of the tracking system 213. The output is shown in axial, sagittal and coronal views as part of a multi-view display.

Still referring to FIG. 2, minimally invasive brain surgery using access ports is a recently conceived method of performing surgery on brain tumors previously considered inoperable. In order to introduce an access port into the brain, an introducer 210 with an atraumatic tip is positioned within the access port and employed to position the access portion within the head. The introducer 210 may include fiducial markers 212 for tracking. The fiducial markers 212 is reflective spheres in the case of optical tracking system or pick-up coils in the case of electromagnetic tracking system. The fiducial markers 212 are detected by the tracking system 213 and their respective positions are inferred by the tracking software.

Still referring to FIG. 2, once inserted into the brain, the introducer 210 is removed to allow for access to the tissue through the central opening of the access port. However, once introducer 210 is removed, the access port can no longer be tracked. Accordingly, the access port is indirectly tracked by additional pointing tools configured for identification by the navigation system 200.

Still referring to FIG. 2, a guide clamp 218 for holding the access port 206 is provided. Guide clamp 218 can optionally engage and disengage with access port 206 without needing to remove the access port from the patient. In some embodiments, the access port can slide up and down within the clamp while in the closed position. A locking mechanism is attached to or integrated with the guide clamp, and can optionally be actuated with one hand, as described further below.

Still referring to FIG. 2, a small articulated arm 219 is provided with an attachment point to hold guide clamp 218. Articulated arm 219 may have up to six degrees of freedom to position guide clamp 218. Articulated arm 219 is attached or attachable to a point based on patient head holder 217, or another suitable patient support, to ensure when locked in place, guide clamp 218 cannot move relative to the patient's head. The interface between guide clamp 218 and articulated arm 219 is flexible, or optionally locked into place. Flexibility is desired so the access port can be moved into various positions within the brain, but still rotate about a fixed point.

Still referring to FIG. 2, an example of such a linkage that can achieve this function is a slender bar or rod. When the access port 206 is moved to various positions, the bar or rod will oppose such a bend, and move the access port 206 back to the centered position. Furthermore, an optional collar is attached to the linkage between the articulated arm, and the access port guide, such that when engaged, the linkage becomes rigid. Currently, no such mechanisms exist in the related art to enable positioning an access port in such a manner.

Figure 3:
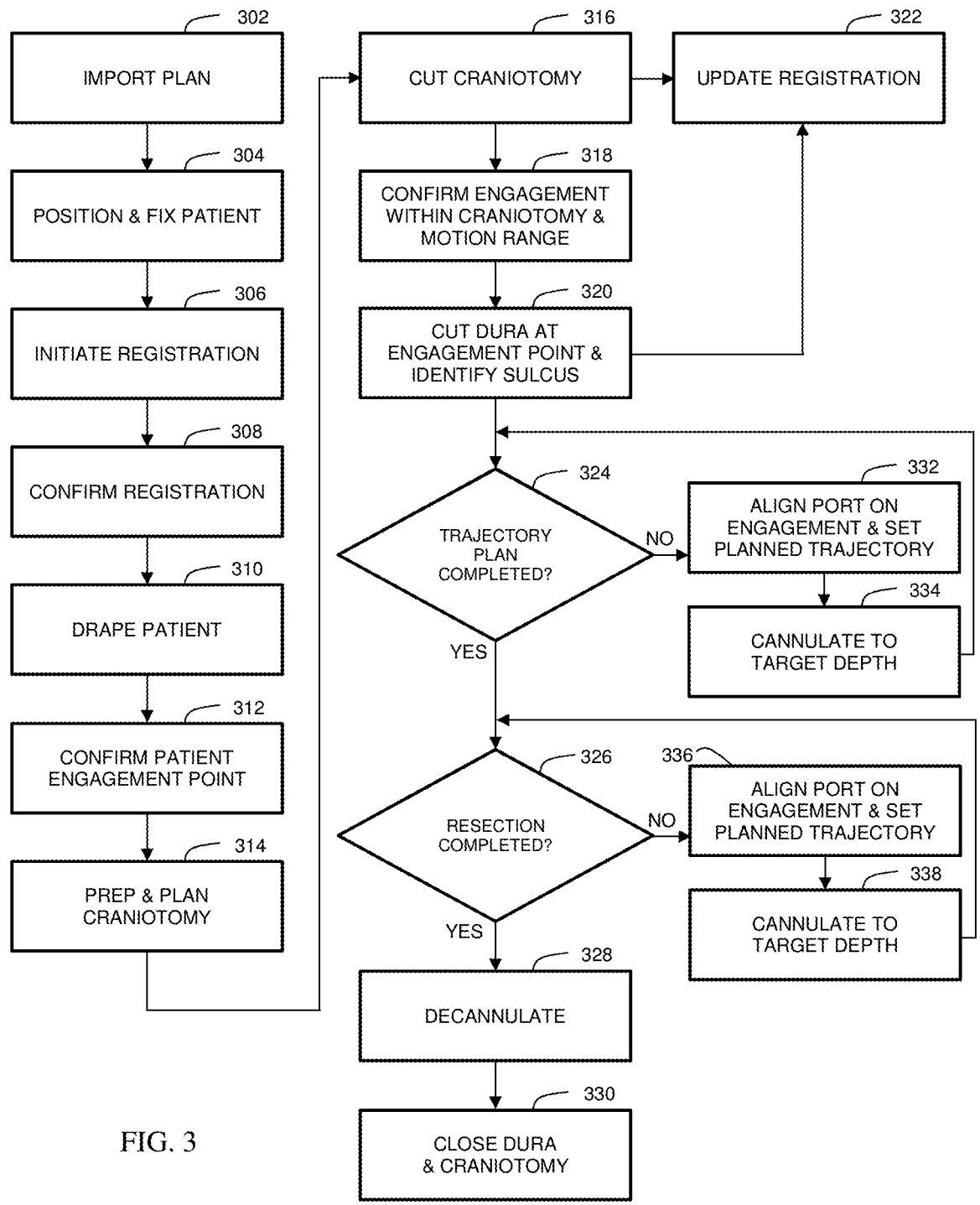
FIG. 3 is a flow diagram illustrating processing steps in a port-based surgical procedure using a navigation system, in accordance with an embodiment of the present disclosure.

Referring to FIG. 3, this flow diagram illustrates the process steps involved in a port-based surgical procedure using a navigation system, in accordance with an embodiment of the present disclosure. The first step comprises importing the port-based surgical plan (step 302). A detailed description of the process to create and select a surgical plan is outlined in PCT Patent Application No. PCT/CA2014/050268, titled "SURGICAL NAVIGATION SYSTEM", which is hereby incorporated by reference in its entirety, and which claims priority to U.S. Provisional Patent Application Ser. Nos. 61/800,155 and 61/924,993, which are both hereby incorporated by reference in their entirety.

Still referring to FIG. 3, an example plan, as outlined above, may compose of pre-operative 3D imaging data, e.g., magnetic resonance imaging (MRI), ultrasound, etc., and overlaying on it, received inputs, e.g., sulci entry points, target locations, surgical outcome criteria, additional 3D image data information, and displaying one or more trajectory paths based on the calculated score for a projected surgical path. The aforementioned surgical plan is one example; and other surgical plans and/or methods may also be encompassed by the present disclosure.

Still referring to FIG. 3, once the plan has been imported into the navigation system (step 302), the patient is affixed into position using a head or body holding mechanism. The head position is also confirmed with the patient plan using the navigation software (step 304).

Still referring to FIG. 3, the next step is to initiate registration of the patient (step 306). The phrase "registration" or "image registration" refers to the process of transforming different sets of data into one coordinate system. Data is multiple photographs, data from different sensors, times, depths, or viewpoints. The process of "registration" is used in the present application for medical imaging in which images from different imaging modalities are co-registered. Registration is necessary in order to be able to compare or integrate the data obtained from these different modalities.

Still referring to FIG. 3, the present disclosure encompasses numerous registration techniques; and at least one technique is used in the embodiments of the present disclosure. Non-limiting examples include, but are not limited to, intensity-based methods which compare intensity patterns in images via correlation metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, for example, a series of MR images can be co-registered, while multi-modality registration methods are used to register images acquired by different scanner/sensor types, for example in MRI and positron emission tomography (PET). In the present disclosure multi-modality registration methods are used in medical imaging of the head/brain as images of a subject are frequently obtained from different scanners. Examples include registration of brain CT/MRI images or PET/CT images for tumor localization, registration of contrast-enhanced CT images against non-contrast-enhanced CT images, and registration of ultrasound and CT.

Still referring to FIG. 3, once registration is confirmed (step 308), the patient is draped (step 310). Typically draping involves covering the patient and surrounding areas with a sterile barrier to create and maintain a sterile field during the surgical procedure. The purpose of draping is to eliminate the passage of microorganisms, e.g., bacteria, between non-sterile and sterile areas.

Still referring to FIG. 3, upon completion of draping (step 310), the next steps is to confirm patient engagement points (step 312) and then prep and plan craniotomy (step 314).

Still referring to FIG. 3, upon completion of the prep and planning of the craniotomy step (step 312), the next step is to cut craniotomy (step 314) where a bone flap is temporarily removed from the skull to access the brain (step 316). Registration data is updated with the navigation system at this point (step 322).

Still referring to FIG. 3, the next step is to confirm the engagement within craniotomy and the motion range (step 318). Once this data is confirmed, the procedure advances to the next step of cutting the dura at the engagement points and identifying the sulcus (step 320). Registration data is also updated with the navigation system at this point (step 322).

Still referring to FIG. 3, in an embodiment, by focusing the camera's gaze on the surgical area of interest, this registration update can be manipulated to ensure the best match for that region, while ignoring any non-uniform tissue deformation affecting areas outside of the surgical field (of interest). Additionally, by matching overlay representations of tissue with an actual view of the tissue of interest, the particular tissue representation can be matched to the video image, and thus tending to ensure registration of the tissue of interest.

Still referring to FIG. 3, for example, video of post craniotomy brain (e.g., brain exposed) can be matched with an imaged sulcal map; the video position of exposed vessels can be matched with image segmentation of vessels; the video position of a lesion or tumor can be matched with image segmentation of tumor; and/or a video image from endoscopy within a nasal cavity can be matched with bone rendering of bone surface on nasal cavity for endonasal alignment.

Still referring to FIG. 3, in other embodiments, multiple cameras can be used and overlaid with tracked instrument(s) views, and thus allowing multiple views of the data and overlays to be presented at the same time, which can tend to provide even greater confidence in a registration, or correction in more than dimensions/views.

Still referring to FIG. 3, thereafter, the cannulation process is initiated (step 324). Cannulation involves inserting a port into the brain, typically along a sulci path as identified in step 320, along a trajectory plan. Cannulation is an iterative process that involves repeating the steps of aligning the port on engagement and setting the planned trajectory (step 332) and then cannulating to the target depth (step 334) until the complete trajectory plan is executed (step 324).

Still referring to FIG. 3, the surgeon then performs resection (step 326) to remove part of the brain and/or tumor of interest. Resection (step 326) is a continual loop including both fine and gross resection (step 336). The next step involves hyperspectral imaging (step 338) which is performed on either fine or gross resection (step 336). Hyperspectral imaging (step 338) is used as a form of tissue differentiation and may assist surgeons to investigate cancerous stem cells. Further, the ability to hyperspectrally image tissue being operated on either as part of an external video scope or as a separate module may provide the ability to perform chemical imaging using the absorption of tissue, the ability to differentiate tissues based on scattering properties, and/or the ability to improve visualization by imaging at wavelengths with reduced absorption or scattering properties.

Still referring to FIG. 3, once resection is completed (step 326), the surgeon then decannulates (step 328) by removing the port and any tracking instruments from the brain. Finally, the surgeon closes the dura and completes the craniotomy (step 330).

Figure 4:
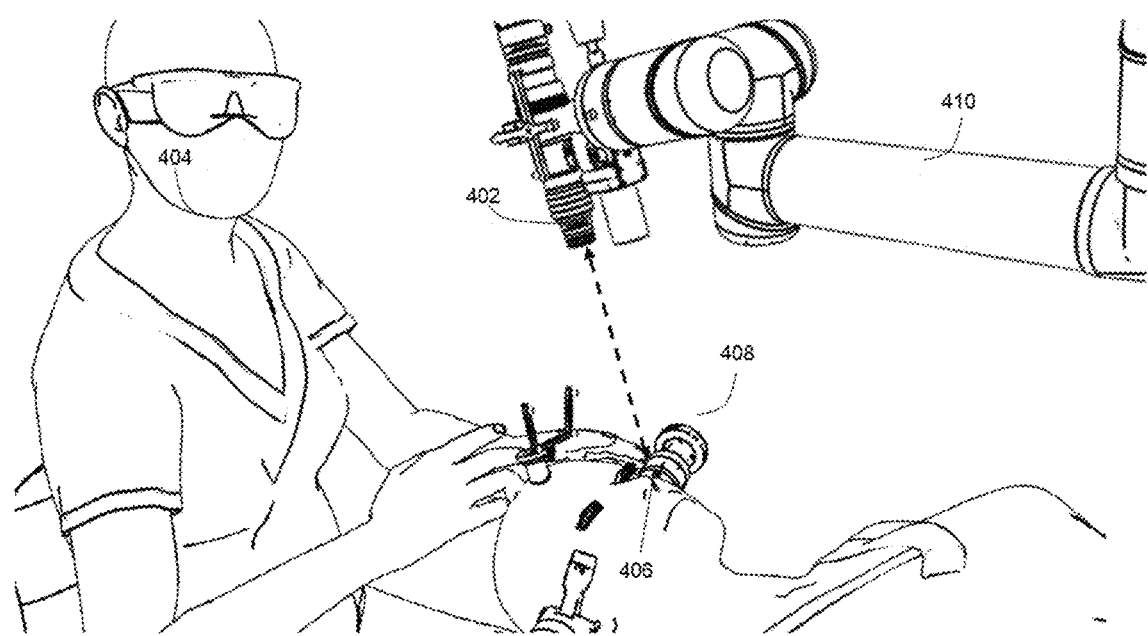
FIG. 4 is a diagram illustrating port based brain surgery using a video scope, in accordance with an embodiment of the present disclosure.

Referring to FIG. 4, this diagram illustrates an example port-based brain surgery procedure using a video scope, in accordance with an embodiment of the present disclosure. An operator 404, typically a surgeon, would align video scope 402 to peer down port 406. Video scope 402 is attached to an adjustable mechanical arm 410. Port 406 may have a tracking tool 408 attached to it where tracking tool 408 is tracked by a tracking system of a navigation system.

Still referring to FIG. 4, even though the video scope 402 is commonly an endoscope or a microscope, these devices introduce optical and ergonomic limitations when the surgical procedure is conducted over a confined space and conducted over a prolonged period such as the case with minimally invasive brain surgery.

Figure 5A:
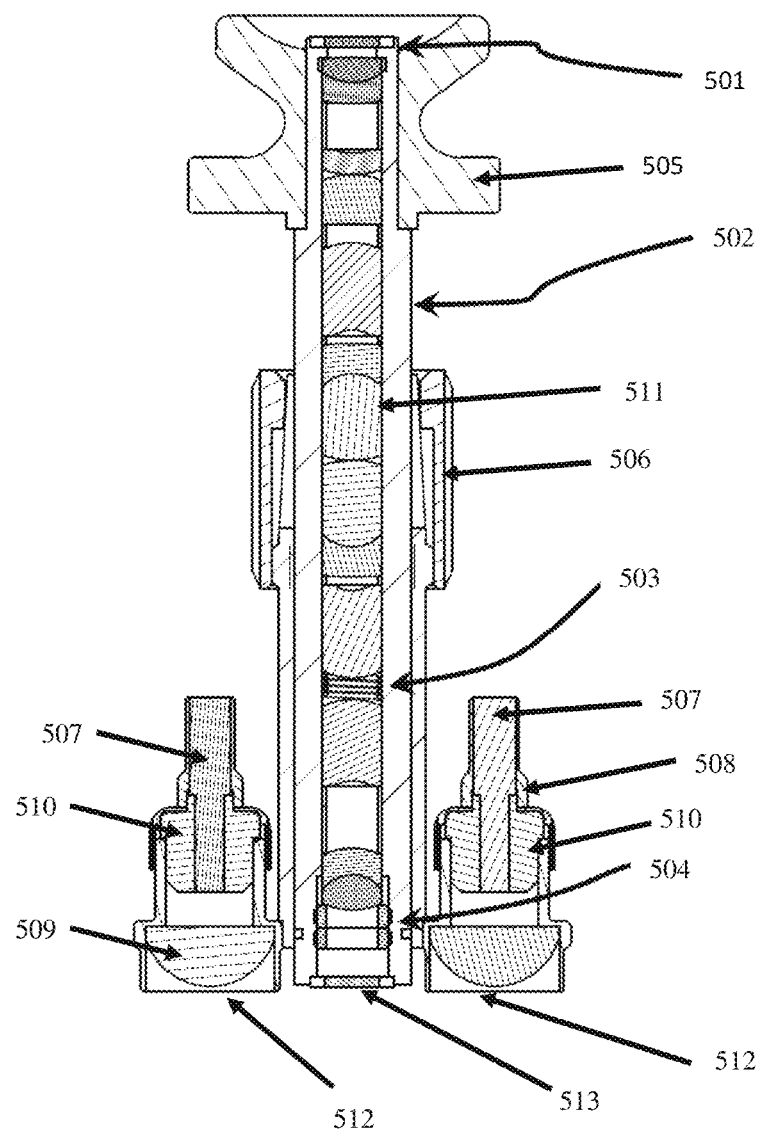
FIG. 5A is a diagram illustrating a video scope with camera coupler and illumination optics, in accordance with an embodiment of the present disclosure.

Referring to FIG. 5A, this diagram illustrates a video scope, comprising a lens assembly 511, described, infra, and two illumination delivery points 512, in accordance with an embodiment of the present disclosure. The lens assembly 511 is terminated at the eyepiece end with a sealed window 501 at the proximal end. A sealed window 501 is typically made of quartz, to help maintain water seal since OR devices must be steam cleanable. The eyepiece end also has a camera coupler 505 that provides a standardized mounting point for a camera (not shown). The camera is a standard definition (SD), high definition (HD) or ultra-high definition (UHD) camera. In another embodiment, the camera is replaced by other imaging technologies such as Optical Coherence Tomography (OCT) or Polarization Sensitive-OCT. The distal end of the lens assembly is also sealed with a clear window 513 at the distal end. The distal end also supports illumination optics 512. In an alternate embodiment the distal end is also optionally affixed with a polarizing filter to enable polarization sensitive imaging.

Figure 5B:
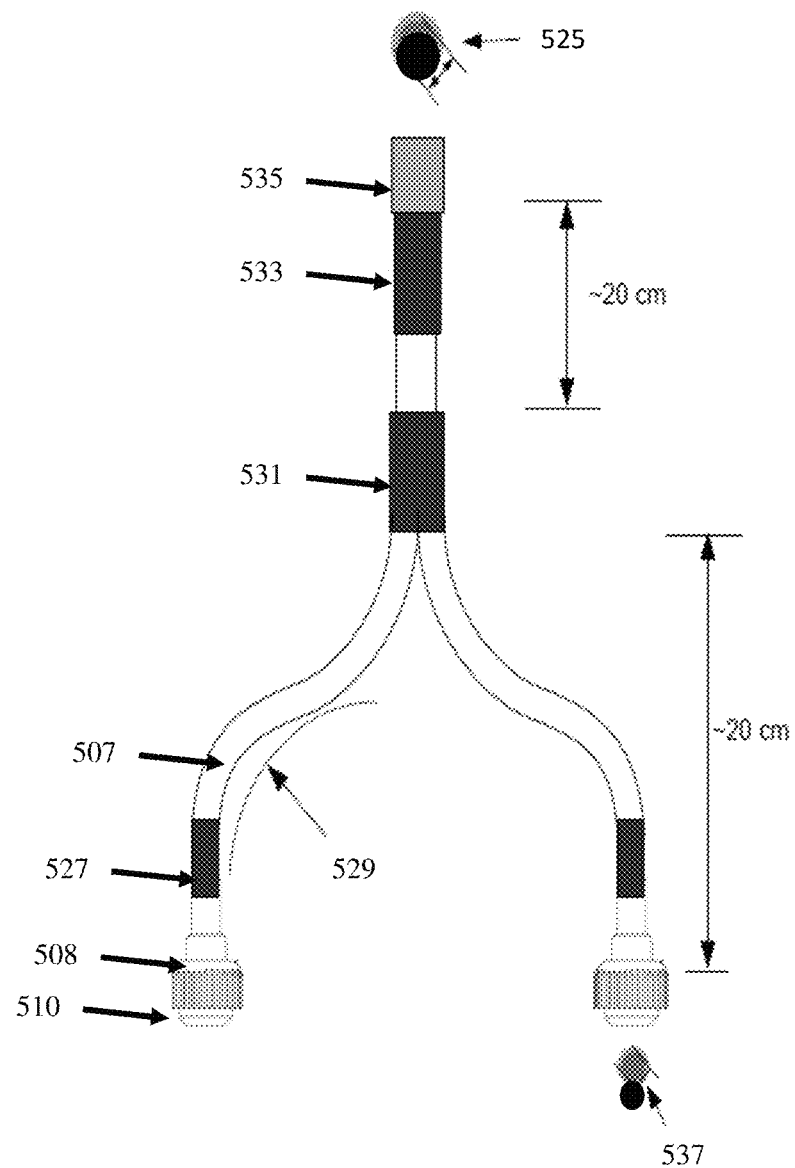
FIG. 5B is a diagram illustrating a fiber bundle used to deliver light from external light source to the video scope, in accordance with an embodiment of the present disclosure.

Referring to FIG. 5B, this diagram illustrates the illumination optics is comprised of fiber bundles 507 that are rotatably attached using a pair of connectors 510, in accordance with an embodiment of the present disclosure. The connectors 510 allow the fiber bundles to rotate freely (570 in FIG. 5C) within the connector while maintaining a fixed distance between the lens 509 and tip of the fiber bundle 507 using a loose sleeve 508. This rotation movement will reduce the strain on the fiber bundle when the video scope is moved on a holding system (not shown) or a mechanical arm 410, as shown in FIG. 4. The rotatable connector 510 also aid in easy cable management when the mechanical arm 410 is moved during a surgical procedure. The illumination optics are placed as close as possible to the objective lens. A non-limiting example of spacing between the optics is approximately 30 mm to approximately 35 mm, or approximately 32 mm to approximately 34 mm, between the center of the lenses 509 where the diameter of lenses 509 is approximately 15 mm. This configuration is optimal for illuminating the bottom of a surgical port with maximum intensity when the distal end of the video scope is between approximately 25 cm to approximately 40 cm from the bottom of the surgical port. An optical compensator 503 is used to act as a thermal compensator to control the stress on optical components during steam cleaning. A holder 506 provides an easy to grasp assembly to hold and manipulate the video scope without introducing mechanical stress on the lens assembly. The lens assembly is encased in a sealed barrel 511 to avoid ingression of steam and liquids during normal use and cleaning. The rotatable attachment mechanism 510 allows free rotation of the fiber bundles when the camera is moved manually or when mounted to a robotic positioning system. This, in turn, avoids undue stress on the fiber bundles that are susceptible to fracture.

Figure 5C:
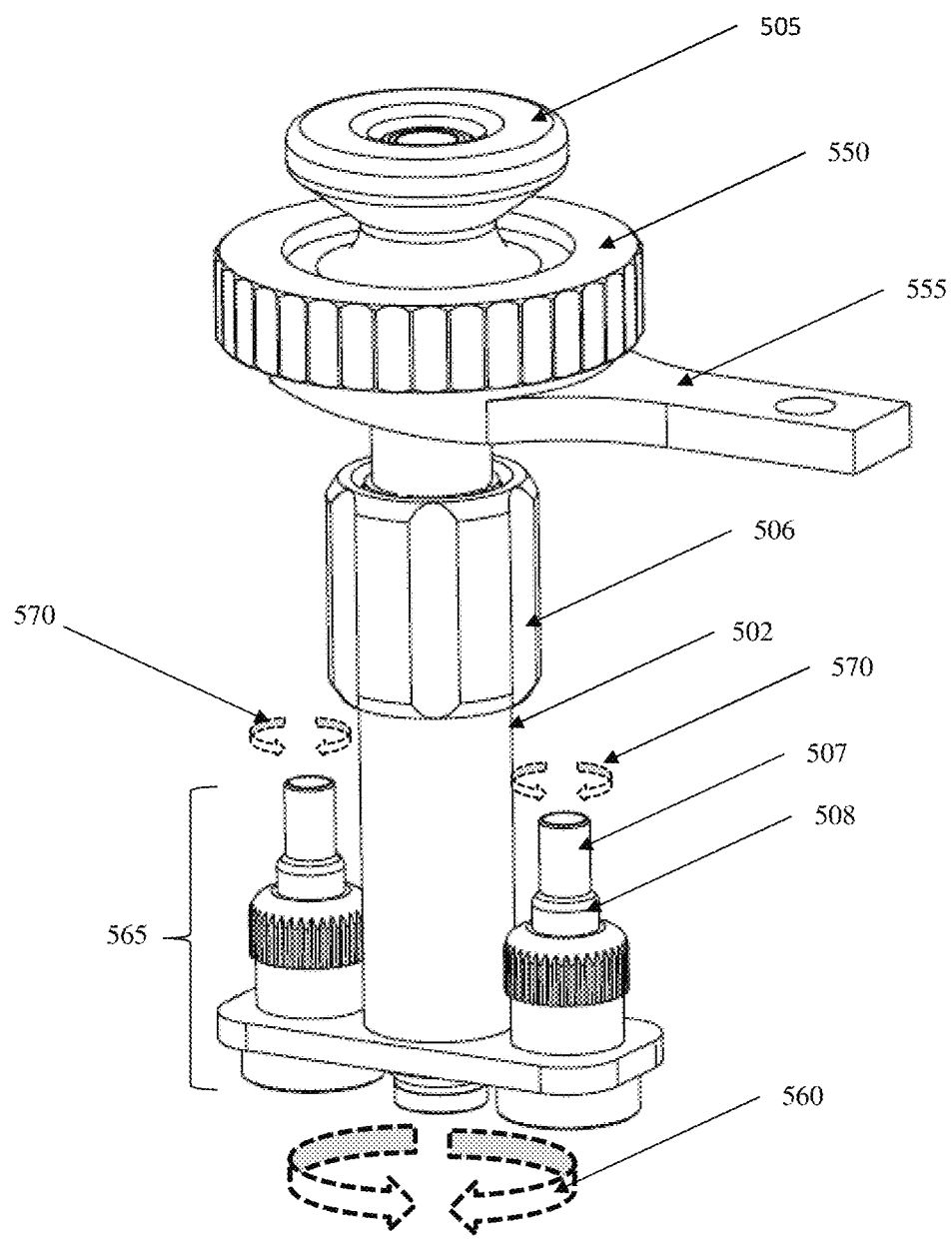
FIG. 5C is a diagram illustrating a video scope and illumination assembly optics, in accordance with an embodiment of the present disclosure.

Referring to FIG. 5C, this diagram illustrates a non-limiting example to realize a functionality that allows the illumination assembly 565 to rotate radially 560 around the video scope barrel 502, in accordance with an embodiment of the present disclosure. The illumination assembly 565 is comprises the two fiber bundles 507 on either side of the video scope, mounting mechanism 508 and lens 509 (as in FIG. 5A). This allows the surgeon to adjust the radial orientation of the illumination and orient the illumination assembly so that it minimally obstructs the surgeon's view of the surgical space. The illumination assembly can be freely rotated without rotating the video scope by securing the video scope to an external positioning mechanism, such as 410, using a removable clamp 555 and an associated lock 550. The removable clamp's distal end 555 and the associated lock 550 is mated together using a thread mechanism or any other mechanical fastening mechanism. The removal clamp's proximal end (not shown) is secured to the external positioning mechanism 410. In this embodiment, the rotation 560, enabled along with the rotation 570 of the fiber bundles within the connectors, enables positioning and orientation of the video scope with minimal interruption of the visible surgical space and minimize strain on the fiber bundles during motion. Finally, the illumination assembly 565 is replaced with alternative configurations, such as ring lights or single illumination points. Ring lights is realized through circular arrangement of fiber strands (not shown) from an optical fiber bundle around the circumference of the objective lens. Single illumination points is realized through removal of one of the two split fiber bundles 507 from the configuration.

Referring back to FIGS. 5A-5C, the illumination assembly preferably receives the light input from an optical source that is located away from the video scope. This reduces the total weight of the external scope and allows for easy manipulation of the video scope by a manual positioning system (not shown) or a mechanical arm 410. The light from the light source is delivered to the video scope through the use of a fiber bundle. Presence of two delivery points represented by illumination optics 512 in FIG. 5A requires the use of a fiber bundle that is split in two. This configuration of fiber bundle is also known as a Y-cables. An example embodiment of this Y-cable configuration is illustrated in FIG. 5B. In FIG. 5B, rotatable connections 508 are provided on the fasteners 510 at the two distal end of the Y cable, providing a mechanism for freely rotating the fiber bundles to avoid fracture of the bundles. A strain-relief 527 helps maintain a minimum limit on the bend radius 529 of the bundle between the two distal ends and the Y-junction 531. Y-junction 531 helps reduce bend strain on the fiber bundle 507. Strain-relief 533 similarly aids in reducing bend strain near the connector 535 at the proximal end of the Y-cable. Cross sections 525 and 537 illustrate fiber bundles at the two ends of the Y-cable. The length of the cable is at least 40 cm with the Y-junction 531 placed equidistant from the two ends. This dimension provides for placement of light source on a cart or instrumentation tower 201 sufficiently away from the mechanical arm 410 while minimizing light loss due to excessive length of the fiber bundle.

Figure 6:
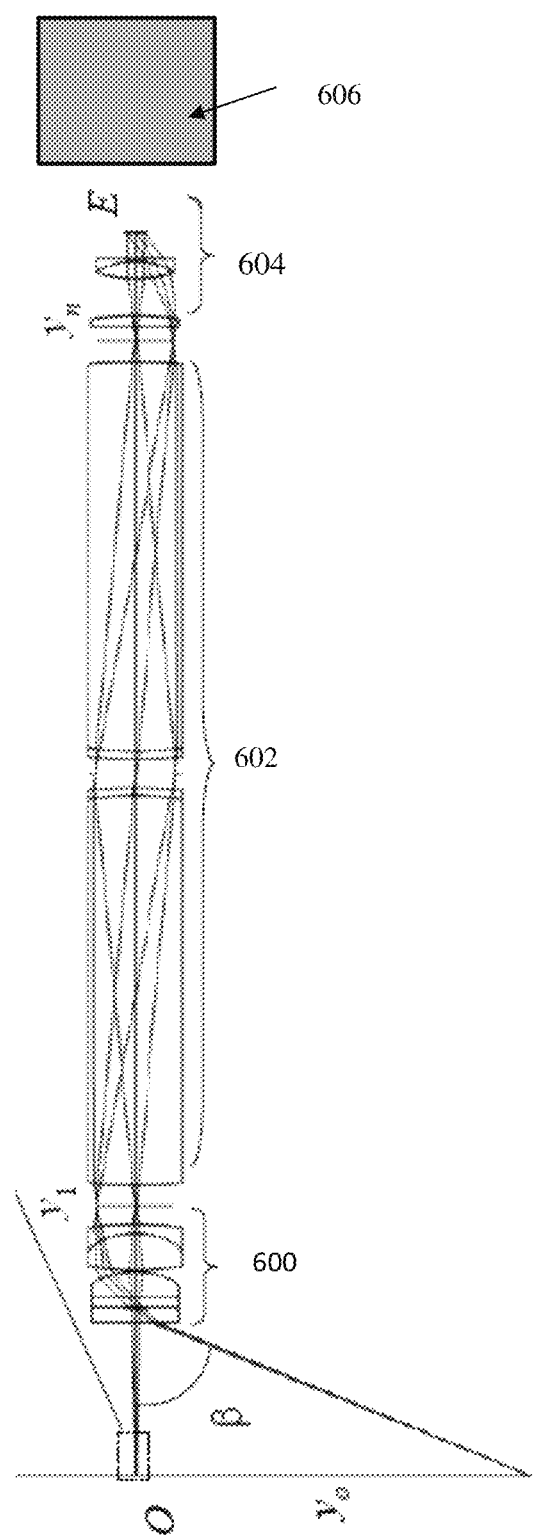
FIG. 6 is a diagram illustrating imaging optical subsystem of the video scope optics, in accordance with an embodiment of the present disclosure.

Referring to FIG. 6, this diagram illustrates an optical configuration of the video scope that limits the diameter of the objective lens 600 (front lens), in accordance with an embodiment of the present disclosure. This configuration enables the mounting of illumination optics immediately adjacent to the objective lens so that the illumination beam can be almost collinear to the return path of the light reflected from the tissue. The illumination beam and the reflected beam need to be as collinear as possible so that maximum illumination is delivered at the bottom of the access port 406. Finally, the optical configuration is constrained so that the length of the lens assembly is minimized to make the whole video scope 402 minimally intrusive to the surgeon's field of view and facilitate easy access to the surgical space by the surgeon. This constraint is a challenge in conventional optical configuration conventional optical configuration techniques maximize zoom by utilizing maximum available physical length of the lens assembly during the configuration process. This optical configuration of the present disclosure is adapted from a conventional endoscopic system that consists of objective lens 600, relay lens 602 and eyepiece 604. The zoom parameter of the optical assembly is chosen such that the minimum field of view, corresponding to maximum zoom, is equal to approximately 13 mm. This dimension is the diameter of the surgical port. The field of view of approximately 13 mm needs to be achieved at a minimum working distance of approximately 25 cm where the minimum working distance is defined as the distance between the distal end of the video scope (402 in FIG. 4) and bottom of the surgical port (406 in FIG. 4). As described in relation to FIG. 5A, a coupler 505 is used to attach a camera at the eyepiece end (marked 'E' in FIG. 6). The optical configuration of the objective comprises 1 doublet and 1 singlet; the relay comprises 1 doublet and 1 singlet and the eyepiece comprises 2 singlet and 1 doublet. Any manufacturing error is compensated using one optical compensator 503 that is placed between the objective and relay. The length of the optical sub-assembly is minimized through the use of higher power lenses and fewer lens groups.

Still referring to FIG. 6, the type of surgical procedure determines either a wide-field of view (WFOV) or a narrow field of view (NFOV) video scope. For example, a neck surgery may benefit from a WFOV video scope where large area is captured by the video scope; whereas, a port-based brain surgery may benefit from a NFOV video scope. Instead of attempting to address both these configuration requirements using one device, two separate configurations is developed such that they share several sub-components and the manufacturing process. Hence, it is economical to manufacture two different configurations while sharing number of configuration elements and assembly procedure. Both WFOV and NFOV configurations share a similar optical illumination system 512 as seen in FIG. 5A, The WFOV configuration can be realized by attaching a camera to the camera coupler 505. The zoom adjustment of the camera is used to determine the field of view in this case.

Figure 7:
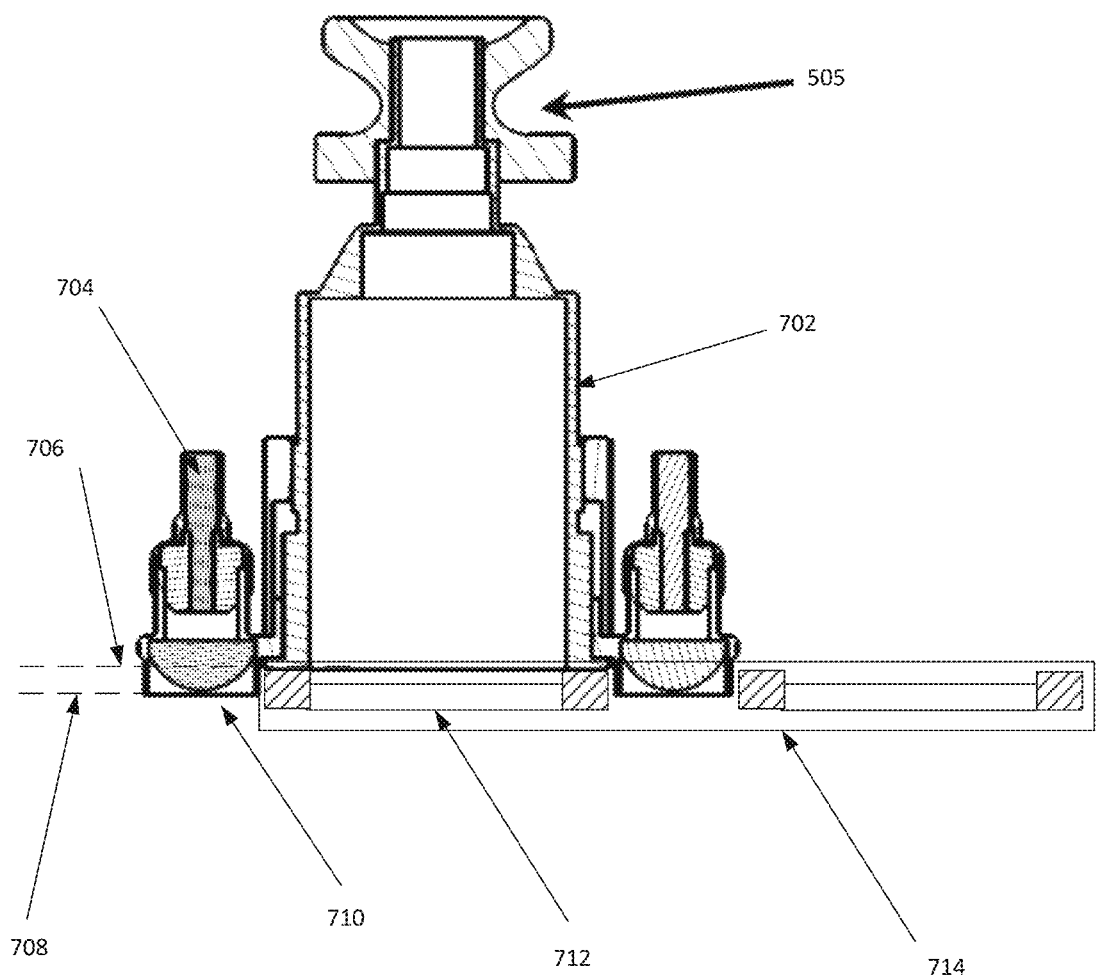
FIG. 7 is a diagram illustrating the arrangement of illumination optics and filter wheel for wide field of view arrangement optics, in accordance with an embodiment of the present disclosure.

Referring to FIG. 7, this diagram illustrates an assembly with a non-coaxial illumination source), in accordance with an embodiment of the present disclosure. The illumination system 710 is similar in configuration to that illustrated in FIG. 5A and consists of fiber bundles 704 (only a distal portion of which are shown in the Figure). An air-filed opaque tube (also known as optical tube) 702 is used to position the illumination mechanism away from the camera attached to the coupler 505. Any required magnification is provided by the camera lens (not shown but typically attached to the camera coupler) for WFOV application. A finite space that is at least 1 mm between the plane 706 of the distal end of the optical tube and the plane of the illumination optics 708 helps isolate the illumination light from directly reaching the camera input. Further, the dimensions of the WFOV optics are such that the illumination will not be nearly coaxial with the path of the reflected light. This is not a limitation in this configuration because WFOV is used to observe a surgical space that is larger that of a port (which is approximately 13 mm). Hence, general illumination is sufficient. Placement of the illumination source close to the camera does improve illumination of the surgical area compared to the use of overhead surgical lights and avoids glare from area outside of the surgical space. The role of additional components, 712 and 714, are explained below in the context of hyperspectral imaging.

Still referring to FIG. 7, in another embodiment of the video scope, the illumination sources placed immediately adjacent to the distal end of the video scope is employ a light source such as luminance light emitting diodes or Super Luminescent Diodes (SLD's) (not shown). Since the light sources are not co-axial to the reflected light path (the light path incident on the lens and camera assembly), the light sources have to be aimed or steered at the focal plane of interest. Such steering is achieved using movable fiber bundle mounts 510 as shown in FIG. 5A.

Figure 8A:
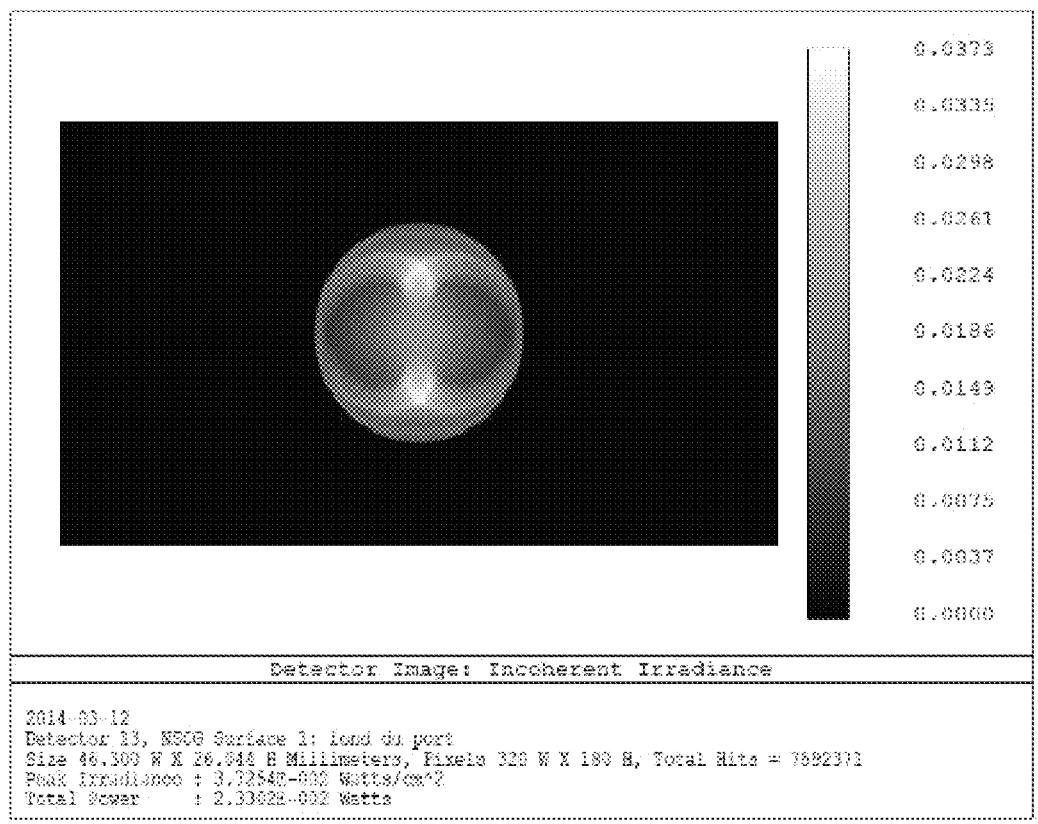
FIG. 8A is a diagram illustrating the non-uniform illumination obtained at the distal end of port with two illumination sources and a port with reflective surface optics, in accordance with an embodiment of the present disclosure.
Figure 8B:
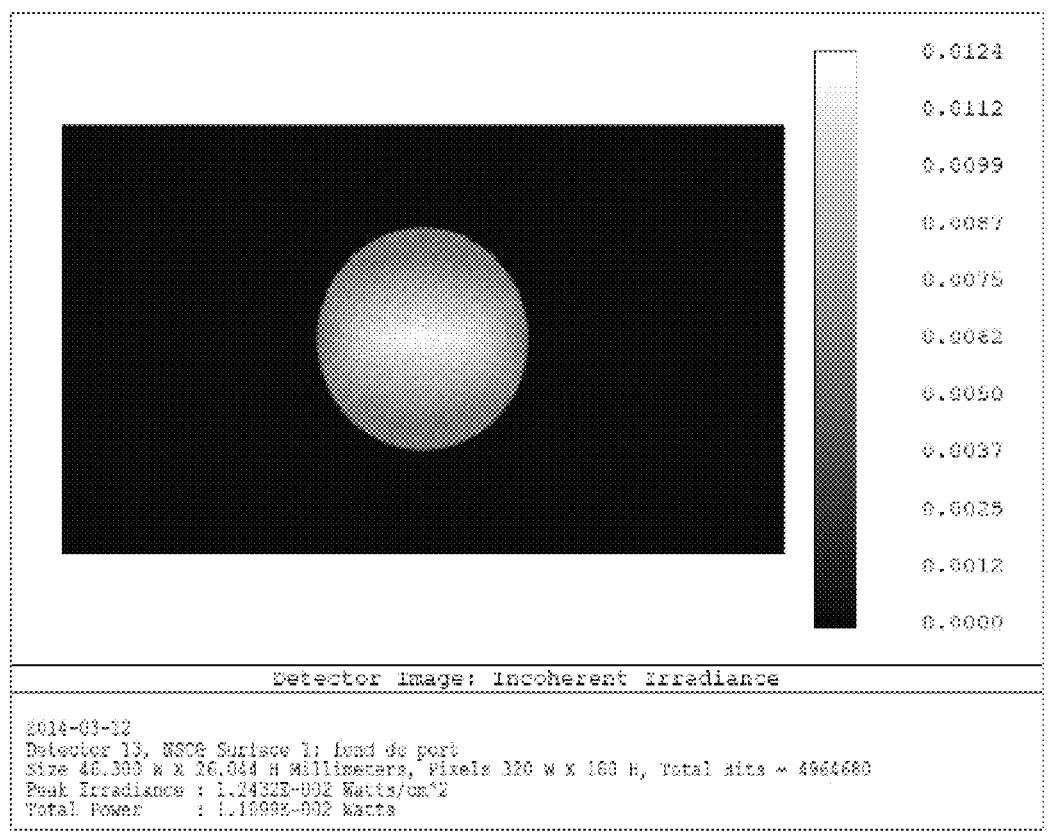
FIG. 8B is a diagram illustrating the near-uniform illumination obtained at the distal end of the port with two illumination sources and a port with rough surface optics, in accordance with an embodiment of the present disclosure.

Referring to FIGS. 8A and 8B, together, these diagrams illustrate implementations of such externally positioned illumination sources in port-based imaging addressing several challenges, in accordance with an embodiment of the present disclosure. First, the walls of the port are either partially or fully reflective. This introduces localized regions in the imaged surface that have higher intensity of incident light. Such regions are referred to as "hot-spots." Avoid such high intensity regions is desirable as these tend to saturate sensors and, hence, limit the dynamic range of the sensors in the camera mechanism. Use of post-processing to normalize intensities is less optimal as saturation of sensors results in information loss that cannot be recovered. Presence of high intensity regions can be reduced through the use of surface textures on the port walls that diffuse the light. The impact of using smooth and rough surface texture on the port walls, as respectively shown in FIGS. 8A and 8B. The reflections resulting from textured walls is referred to as Lambertian reflection. The assessment, shown in FIGS. 8A and 8B, were conducted using ray-tracing tools and the resulting intensity of light at the surface of the tissue (distal end of the port) were visualized using heat-maps or pseudo-color where high intensity corresponded to white and low intensity corresponded to black.

Still referring to FIGS. 8A and 8B, together, another approach to uniformly illuminating at the bottom of the port is to model the light rays using a commonly known optical modelling method, such as ray tracing, and establish the optimal orientation of the light sources that minimize hot-spots at the bottom of the surgical port. Orientation of the light sources is modified using a beam steering mechanism, as shown in FIG. 5A. Alternatively, a robotic positioning system is used to achieve this steering.

Still referring to FIGS. 8A and 8B, together, port-based imaging is also limited by highly reflective nature of some but not all regions of the brain tissue due to the presence of blood, cerebrospinal fluid (CSF), or other fluids. In the latter case, an initial image could be acquired to identify regions with high intensity reflected light and this information can be used to reposition direction of the light sources in an attempt uniformly distribute the incident light. As described above, imaging using white light has several challenges in the operating room. Several of these challenges can be overcome by limiting the spectral range of the light that is observed or by judiciously combining selected wavelength bands to visualize human tissue in the operating room.

Figure 9:
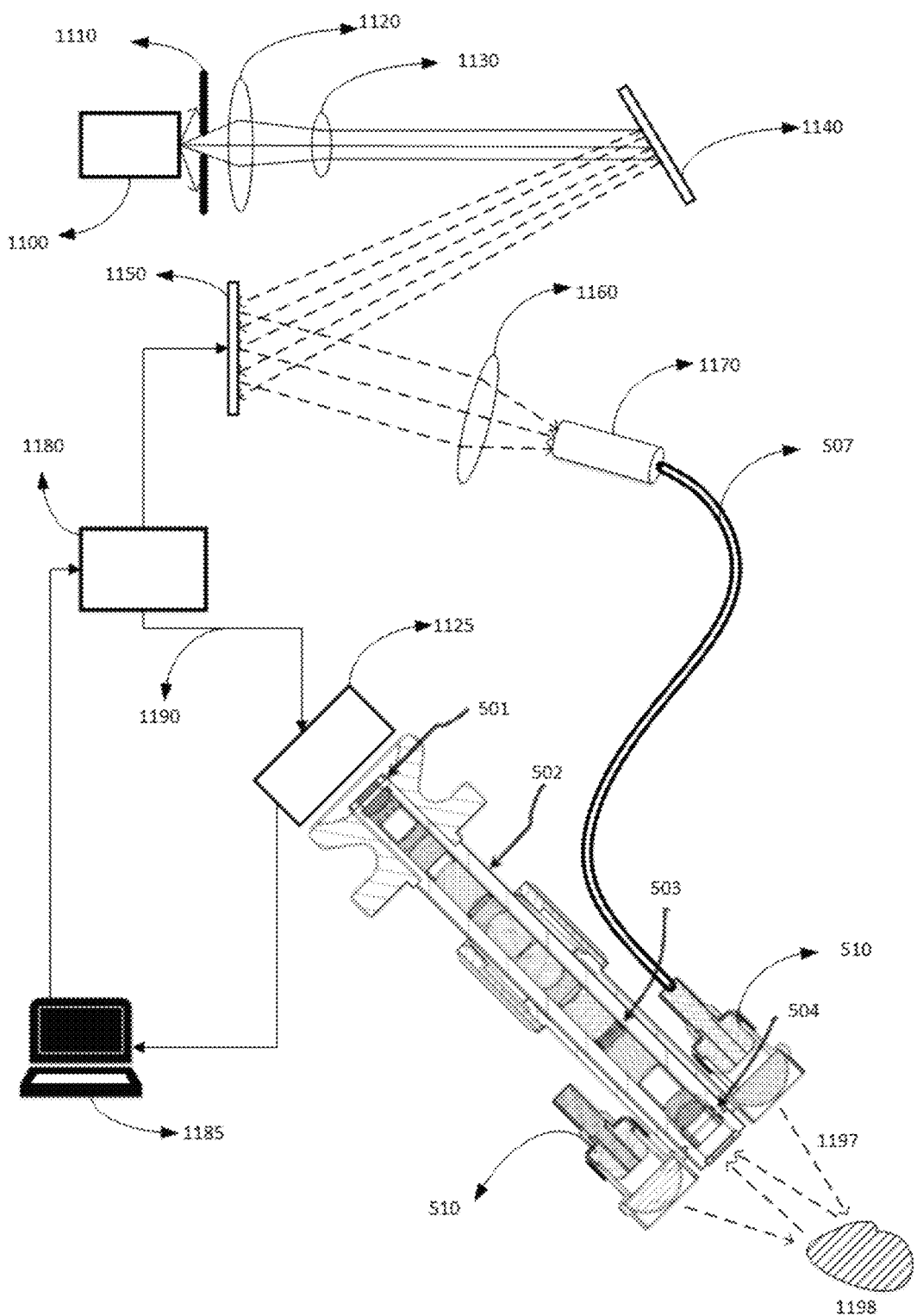
FIG. 9 is a diagram illustrating a standard hyperspectral imaging system optics, in accordance with an embodiment of the present disclosure.

Referring to FIG. 9, this diagram illustrates a video scope that has been adapted to accommodate hyperspectral imaging capabilities, in accordance with an embodiment of the present disclosure. In this embodiment, tunable light source that is adapted based on the surgical context, e.g., selection of illumination spectral region where blood is highly absorptive (to detect blood clots) or transmissive (to avoid excessive light scattering) is used.

Still referring to FIG. 9, the tunable light source mainly comprises a broadband light source 1100, a spectral separation mechanism 1140, a spectral filtering mechanism 1150 and a mechanism to combine the filtered frequency bands 1170. The combining mechanism consists of a lens and a fiber bundle that mixes all the reflected wavelength bands into one beam that is transmitted through the fiber bundle 507. The light from light source 1100 is passed through a slit 1110 to generate a narrow beam. This light is then collimated using optical elements 1120 and 1130. The collimated beam is then split into its spectral components using a prism (not shown), reflective or transmission grating.

Still referring to FIG. 9, further illustrates the use of a reflective grating 1140. The spatially separated beam is filtered by selectively reflecting portions of the spatially separated beam. This is achieved using a spatial light modulator (SLM) 1150, such as a Digital Light Processor® (Texas Instruments, Inc.). An SLM comprises an array of micro-mirrors that can be electronically activated to act as mirrors or deactivated to acts as opaque surfaces. Hence, specific portions of the spectrum are reflected while other regions are suppressed based on the pattern of activated micro-mirrors. The beam that is now comprises selective portions of spectrum are combined using focusing optics 1160 and a combiner 1170.

Still referring to FIG. 9, the recombined beam now comprises only those wavelengths that were selectively reflected by the spatial light modulator, SLM 1150. This light can be used as the illumination source of an imaging system or external scope by transmitting the light via a light pipe 507 to the illuminator connector and lens mechanism 510 attached to the external scope. The video scope illustrated in FIG. 9 shows the connection of light pipe 507 to only one of the two illuminator connectors 510 for the sake of simplicity of the illustration. Details of connecting the light pipe to the video scope is below-described in relation to FIG. 5A.

Still referring to FIG. 9, the reflected light from the tissue 1198 is captured by the external scope that is comprises lens assembly 502. As detailed in FIG. 5A, the lens assembly is composed; this light is captured using a high resolution detector 1125 that is usually a charge coupled device (CCD). The specific band of wavelengths that are reflected by the SLM are controlled by an SLM controller 1180 that is under the command of a computer 1185. The same computer is used to acquire the image from the detector 1125. Hence, the computer can synchronize the illumination of a material 1198 with a specific wavelength band or wavelength bands of light and acquire corresponding reflected light. This association of illumination wavelength and acquired image can be used to construct a hyper-spectral image where each image is a 2D or 1D image and the third dimension is an index that corresponds to illumination wavelength band(s). Since the individual micro-mirrors located in an SLM can be operated at a rate as high as 4 kHz, subsequent frames of the field of view can be obtained at different wavelength bands.

Still referring to FIG. 9, further, some of the acquired frames can be for employed white-light illumination of the tissue. This is possible by operating the acquisition camera at a frame rate that is sufficiently high to provide smooth video playback, as perceived by a human observer when white light frames are intermittently obtained while collecting hyperspectral image frames. For example, in some non-limiting examples, the frame rate is selected to be higher than 20 frames per second, higher than 24 frames per second, or higher than 30 frames per second, in order to support white light video acquisition at such frame rates while obtaining hyperspectral data. For example, at a camera frame rate higher than 20 fps, a white-light image can be acquired every $1/20^{th}$ of a second and any additional frame can be allocated for acquisition using specific wavelength bands. A white light video feed may then be separately generated and displayed based on the collected white light images. This allows the surgeon to continuous view a white-light image of the surgical area while acquiring any additional images at different wavelength bands in a multiplexed manner. The white-light image stream (or video) is viewed in one display or sub-section of a display and other images acquired using other wavelength bands is viewed in a second display or second sub-section of the same display.

Still referring to FIG. 9, the individual wavelength bands comprise non-overlapping individual wavelength bands or combination of bands that may overlap. Alternatively, at least one of the acquired frame can correspond to illumination 1197 of the subject material 1198 using the entire wavelength band of the light source. The entire wavelength band could be also normalized to ensure that all the intensity in the output light emanating from the combiner 1170 is consistent across the entire spectrum. This is known as white balancing. In summary, the same optical mechanism is used to acquire hyperspectral images and white-light images that are interspersed among each other in the acquired sequence of images. This embodiment eliminates the need for splitting the acquired beam into separate paths so that one beam is captured by a hyperspectral imaging system while the other beam is captured by a white-light camera. This reduces the configuration complexity of the optical system and aids in making the system more compact as the spectral shaping part of the system can be separated from the imaging system using a light pipe to channel the output light from the light source. The sample being imaged 1198 is an ex-vivo tissue sample or portion of the brain tissue that is exposed through a port-based neurosurgical access inserted in the skull.

Figure 10:
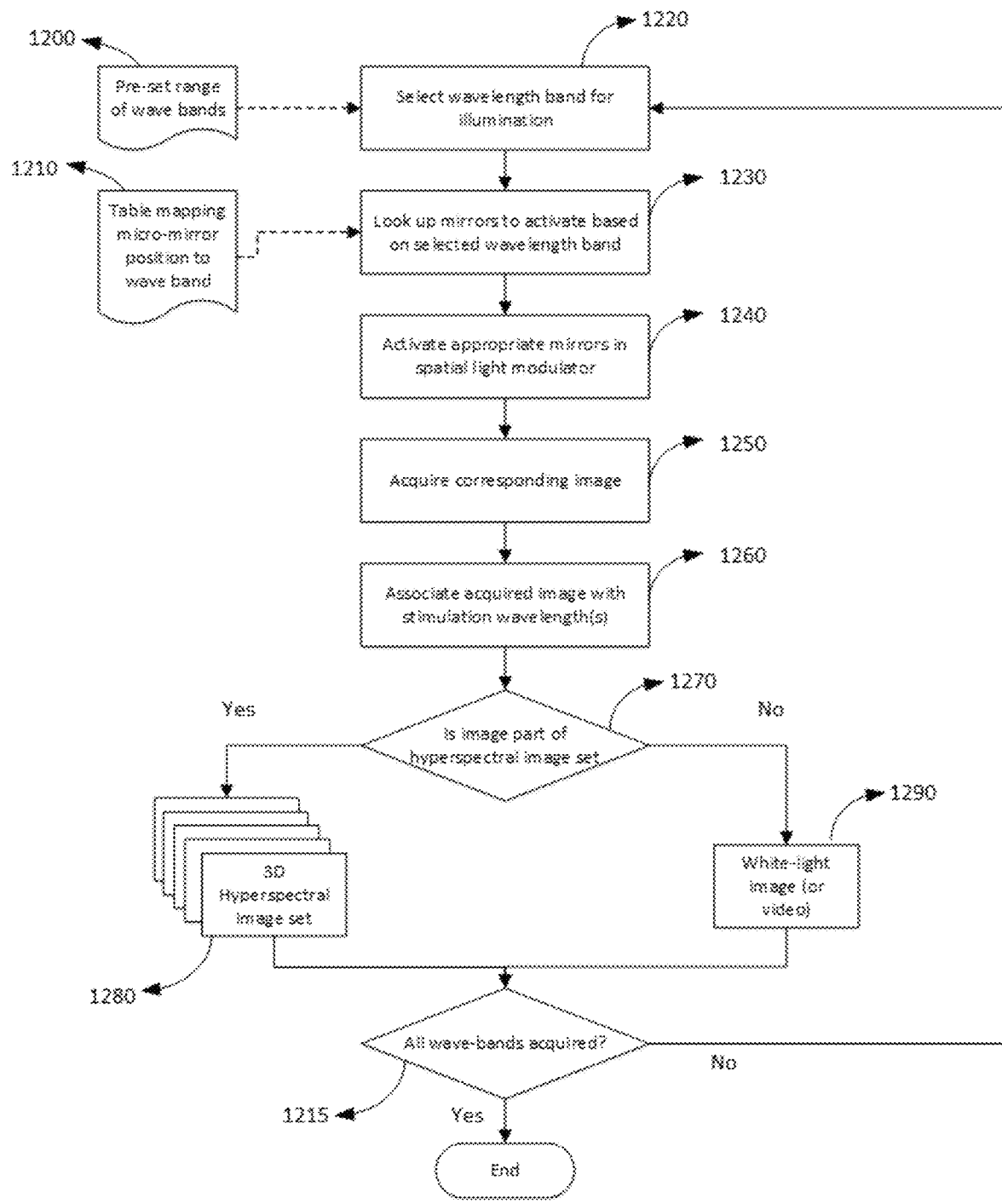
FIG. 10 is a flow diagram illustrating a method to acquire hyperspectral data and white-light images in a multiplex fashion optics, in accordance with an embodiment of the present disclosure.

Referring to FIG. 10, this diagram illustrates the software system used to acquire hyperspectral data and white-light images (or video) in a multiplex fashion, in accordance with an embodiment of the present disclosure. First the range of wavelengths (wave bands) that are of interest are stored in a table (step 1200). Then, specific wave band for illumination is selected from the table (step 1220). Each entry in this table is used to look up (step 1230) specific micro-mirrors that need to be activated using another table (step 1210). Hence, only the micro-mirrors associated with specific wavelength bands are activated (step 1240). Activation of a micro-mirror turns it into a micro-reflector instead of an opaque surface. Hence, the sample 1198 (FIG. 9), is illuminated with the light 1197 (FIG. 9), comprising specific wavelength bands. The table (step 1200) may also include entries that activate the entire spatial light modulator (SLM). In this case, the SLM acts as a mirror for the entire bandwidth of the light source and the acquired image will correspond to white-light illumination.

Still referring to FIG. 10, the reflected light from the illuminated sample is acquired (step 1250) by the same computer and associated with the specific wavelength band (step 1260). The type of illumination (white-light versus specific wavelength band) used for each acquired image is interrogated (step 1270) in order to appropriately classify the acquired image as part of white-light image (video) or part of the hyperspectral image data set. If the acquired image corresponds to a narrow wavelength band then it is stored as part of the hyperspectral image set (step 1280). If the image corresponds to white-light illumination, it is stored as white-light image or a stream of such images is captured to represent a video stream. This acquisition is repeated (step 1215) until all the wavelength bands of interested are sequentially used to illuminate the sample material. Hence, the resulting image set comprises both hyperspectral image sets (step 1280) and white-light image sets (step 1290), all acquired using the same hardware.

Still referring to FIG. 10, ideally, the video stream needs to be at least 30 frames per second to provide a flicker-free video to the surgeon. If a total of 40 frames are acquired per second, the additional 10 frames is used to store images corresponding to 10 distinct or overlapping wavelength bands. Hence, if the total frame rate of the acquisition system is n frames per second, n–30 frames is allocated towards n–30 wavelength bands in the hyperspectral image data set.

Still referring to FIG. 10, an alternative to tunable light source 1110 shown in FIG. 9 is monochromatic, spanning ultraviolet (UV), visible, and/or near infrared (NIR) wavelengths, continuous wave or pulsed that is used to illuminate the tissue using free space or fiber coupled mechanism.

Still referring to FIG. 10, in another embodiment, specific wavelength bands is acquired by filtering the reflected light from a broadband light source using such spectral elements as discrete wavelength filters (on filter wheel or spatial on-chip filters), liquid crystal filters, spectrographs/spectrometers/spectral gratings, spatially varying gratings, fiber-coupled spectrometers.

Referring back to FIGS. 7, 9, and 10, this diagram also illustrates the implementation of discrete filters 712 attached to a rotatable filter wheel 714 that is motorized. This filter mechanism is attached at the distal end of the video scope. Another alternative to discrete filters at the input to the video scope is a liquid crystal-based tunable wavelength filter (not shown) to pass only a narrow range of wavelengths. This filter can be tuned to a number of different wavelengths and operates in a similar manner to the discrete filters as an image is acquired for each wavelength the filter is tuned to. In yet another embodiment, diffraction grating based systems that separate input light input its constituent wavelengths is used in lieu of the camera 1125, as shown in FIG. 9. Imaging spectrometer systems rely on scanning the entrance slit of the system across the field to be imaged. Thus, the acquisition time is limited by the scanning time. The entrance slit of the spectrometer can be either free space or fiber coupled to the optical path. If an array-to-line fiber mapping is utilized, simultaneously acquiring all spatial and spectral information is possible. The spectrometer could be alternatively equipped with Spatially Varying Gratings where a specialized diffraction grating that allows for the collection of spectra from all pixels in a single acquisition. The grating is divided into a number of spatial gratings each with a varying direction of diffraction. An image is acquired that captures the diffracted light from each of these grating regions, this image is then reconstructed to form the hyperspectral data set.

Still referring back to FIGS. 7, 9, and 10, non-limiting examples of camera 1125 comprises at least one of: a monochrome video camera with resolution up to high definition (HD) or ultra-high definition (UHD), a CCD device, a CMOS device, an indium gallium arsenide (InGaAs) device, and a mercury cadmium telluride (HgCdTe) device.

Still referring back to FIGS. 7, 9, and 10, another aspect of confocal hyperspectral imaging system is that the entire tissue surface does not have to be scanned in a raster pattern. Instead, random spots can be accumulated until a reasonable match is found against pre-defined data classes. This can significantly reduce the data acquisition time associated with hyperspectral imaging.

Referring back to FIGS. 1-10, in some embodiments, the hyperspectral imaging system illuminates the tissue with monochromatic or broadband light, collects light reflected from the tissue, controls the wavelength of the detected light in such a way that a series of images, each recorded at different wavelengths or wavelength ranges, is collected. This series of images, known as a hyperspectral dataset, is processed to extract tissue's bio-chemical or microstructural metrics and reduced to 2D (spatial). This reduced 2D image is spatially registered and can be overlaid on the external video scope image as well as any other pre- and intra-operative images. For example, methods of correlating image data are disclosed in PCT Patent Application No. PCT/CA2014/050268, titled "INTRAMODAL SYNCHRONIZATION OF SURGICAL DATA" and filed on Mar. 14, 2014, the entire contents of which are incorporated herein by reference. Spatial registration is realized by using navigation markers attached directly on the camera or on structures rigidly and consistently attached to the camera. This provides both location and orientation of the imaging system. This is further explained in the disclosure related to automated guidance of imaging system.

Referring back to FIG. 10, the hyperspectral dataset 1280 is then processed to extract the tissue specific information and reduce the dimensionality of the data. Tissue specific information can range from tissue type identification to inferring pathology associated with a region of the acquired image. Examples of the possible processing methods follow.

Referring back to FIGS. 1-10, in one embodiment, if the spectral peaks or features of chemical(s) of interest are known, the spectra and be processed, through either peak or feature detection algorithms, to detect the peaks or features to give an indication of the chemical presence and some indication of the concentration or quality. This useful only if the specific chemicals of interest are known.

Still referring back to FIGS. 1-10, in one embodiment, the spectra of specific tissues or tissue states of interest can be acquired and stored in a database, as disclosed in disclosed in PCT Patent Application No. PCT/CA2014/050268, titled "INTRAMODAL SYNCHRONIZATION OF SURGICAL DATA" and filed on Mar. 14, 2014. Spectra then acquired during the surgery can be compared to the spectra stored in the database for similarity and if sufficiently similar to give an indication of what tissue or tissue type the spectra was acquired from.

Still referring back to FIGS. 1-10, multivariate/chemometric methods, which are a wide grouping of statistical techniques where a method is trained on spectra collected from samples with known states, e.g., spectrum and corresponding chemical level, tissue type, tissue state, etc., is used to predict the state of a new sample based on the acquired spectrum. Some of the more commonly used employed techniques include principal component regression (PCR), partial least squares (PLS), and neural networks (NN).

Still referring back to FIGS. 1-10, the aforementioned analysis methods can be implemented in a computer system, and hence the results of the analysis can be obtained in near-real time for appropriate use by a surgeon. This may significantly reduce the need for similar analysis by a pathologist and reduces the wait time associated with obtaining results of such tissue analysis. Correlation metrics between newly acquired data and representative data in a knowledge-base (or database or training set) provide the surgeons a means of quantifying tissue types. Such metrics is a representation of confidence associated with automated inference provided by the software algorithm.

Still referring back to FIGS. 1-10, finally, the ability to selectively view narrow bands of the spectra or reject narrow bands of the spectra may allow the surgeon to reject bright reflections from blood. Hence, the surgeon is able to view the interior of the corridor and proceed with surgical resection of tumor even when the corridor is occluded by excessive bleeding. This will reduce the need to constantly irrigate the narrow corridor and hence reduce interruption of the surgical procedure.

Still referring back to FIGS. 1-10, the embodiments provided herein may employ software to process the 3D dimensional data sets to extract the information of interest, and to reduce the data to a 2D image that can be visualized in conjunction with or overlaid on the surgical image acquired by the external video scope. These software methods could include everything from simple spectral peak detection to more sophisticated multivariate, chemometric, and data mining techniques to extract the metric of interest from the acquire spectra. The spectrum associated with each pixel is processed according to such methods.

Still referring back to FIGS. 1-10, as hyperspectral imaging is an optical technique and limited penetration (~2 mm-~3 mm), its use is restricted to superficial tissues or those exposed through corridor surgery. The unique spectra of chemicals in tissue provide the potential to use hyperspectral imaging to image chemical content and from this provide useful qualitative or quantitative information to the surgeon to assist in decision making during the surgery. Chemical imaging can be used to differentiate between different tissues based on differing chemical composition and associated differing absorption, e.g., white vs grey matter, determine tissue state, e.g., normal vs malignant, and determine tissue status and/or health, e.g., state of oxygenation. The difference in spectral scattering properties can, similar to absorption changes, be used to determine the properties of tissue based on changes in cellular structure with tissue type, e.g., fat vs nerve fiber, and state, e.g., changes in nuclear and overall cell size with pre and cancerous states. Lastly, as the acquired hyperspectral data set contains data acquired at a variety of wavelength, images at only selected wavelengths or wavelength ranges to improve the visualization of tissue (minima or maxima in absorption or scattering). For example, images at wavelengths where hemoglobin absorption is at a minimum, the absorption due to blood will be significantly reduced thus providing additional light for illumination.

Figure 11:
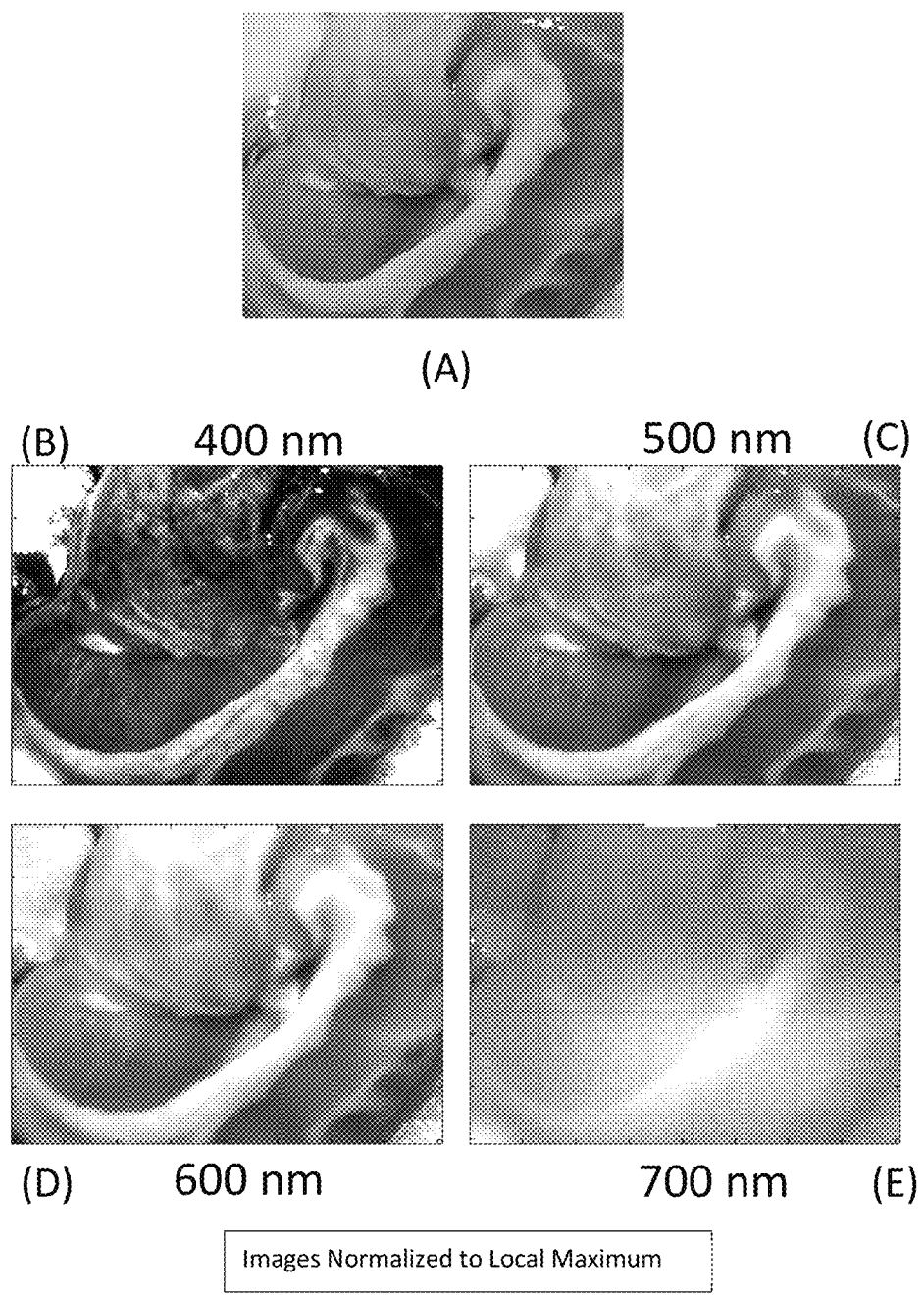
FIG. 11 is a diagram illustrating imaging at specific wavelength bands optics, in accordance with an embodiment of the present disclosure.

Referring to FIG. 11, this diagram illustrates an advantage of imaging at specific wavelength bands, in accordance with an embodiment of the present disclosure. A standard color image (A) of a brain region (Corpus Callosum) that is also captured using four different wavelength bands centered at 400 nm (B), 500 nm (C), 600 nm (D) and 700 nm (E) and a bandwidth of 10 nm each. The 400-nm filter band clearly illustrates tissue structures that are otherwise invisible in other wavelength bands.

Figure 12:
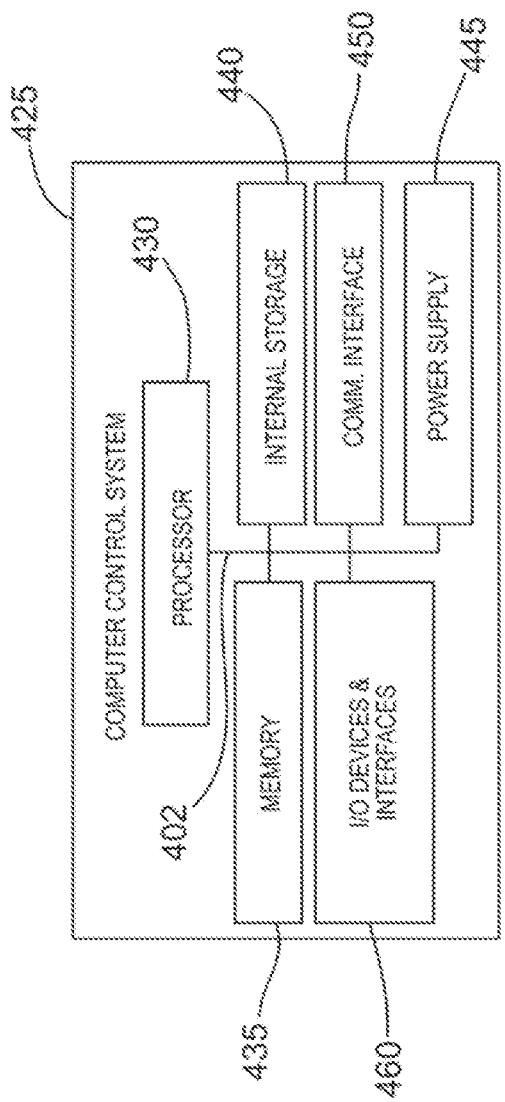
FIG. 12 is a diagram illustrating non-limiting implementation of computer control system optics, in accordance with an embodiment of the present disclosure.

Referring to FIG. 12, this diagram illustrates the key components of the computer system 1185, as shown in FIG. 9, in accordance with an embodiment of the present disclosure. An example of a non-limiting implementation of a computer control system 425 comprises one or more processors 430, e.g., a central processing unit (CPU), a microprocessor, bus 402, memory 435, e.g., a random access memory (RAM) and/or read only memory (ROM), one or more internal storage devices 440, e.g., a hard disk drive, compact disk drive or internal flash memory, a power supply 445, one more communications interfaces 450, and various input/output devices and/or interfaces 460 such as a user interface for a clinician to provide various inputs, run simulations etc.

Still referring to FIG. 12, although only one of each component is illustrated, any number of each component can be included computer control system 425. For example, a computer typically contains a number of different data storage media. Furthermore, although bus 402 is depicted as a single connection between all of the components, the bus 402 may represent one or more circuits, devices or communication channels which link two or more of the components. For example, in personal computers, bus 402 often includes or is a motherboard.

Still referring to FIG. 12, in one embodiment, computer control system 425 is, or include, a general purpose computer or any other hardware equivalents configured for operation in space. Computer control system 425 may also be implemented as one or more physical devices that are coupled to processor 430 through one of more communications channels or interfaces. For example, computer control system 425 can be implemented using application specific integrated circuits (ASIC). Alternatively, computer control system 425 can be implemented as a combination of hardware and software, where the software is loaded into the processor from the memory or over a network connection.

Still referring to FIG. 12, in another example embodiment, a vertical slit or a focal point is imaged by the video scope using a confocal optical configuration that is commonly used in a microscope (not shown). The spot or slit is then imaged on a photomultiplier to generate a very sensitive hyper-spectral imaging system. The focal point is swept across the sample surface using a scanning mechanism, e.g., a galvanometer mirror system.

Figure 13:
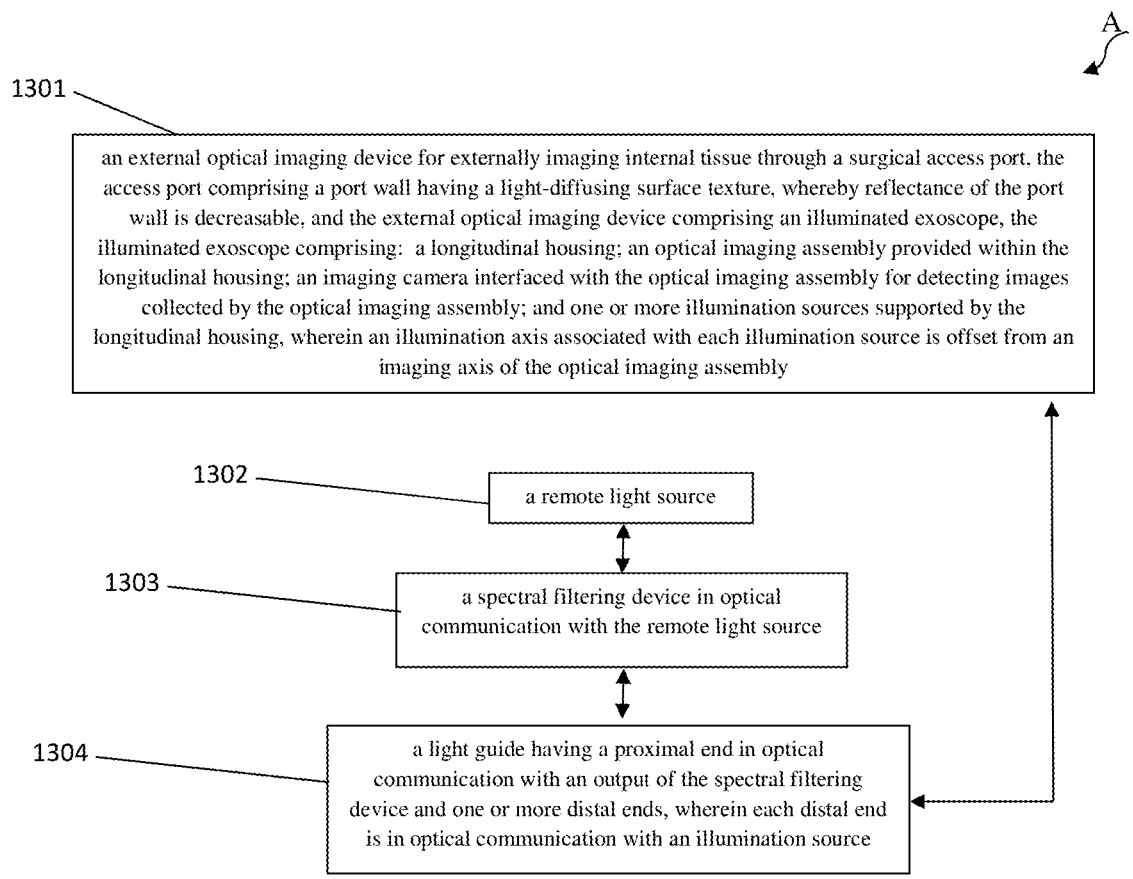
FIG. 13 is a diagram illustrating a hyperspectral imaging apparatus for performing hyperspectral imaging of a surgical field, in accordance with an embodiment of the present disclosure.

Referring to FIG. 13, this diagram illustrates a hyperspectral imaging apparatus A for performing hyperspectral imaging of a surgical field, in accordance with an embodiment of the present disclosure. The apparatus A comprises: an external optical imaging device 1301 for externally imaging internal tissue through a surgical access port, the access port comprising a port wall having a light-diffusing surface texture, whereby reflectance of the port wall is decreasable, and the external optical imaging device comprising an illuminated exoscope, the illuminated exoscope comprising: a longitudinal housing; an optical imaging assembly provided within the longitudinal housing; an imaging camera interfaced with the optical imaging assembly for detecting images collected by the optical imaging assembly; and one or more illumination sources supported by the longitudinal housing, wherein an illumination axis associated with each illumination source is offset from an imaging axis of the optical imaging assembly; a remote light source 1302; a spectral filtering device 1303 in optical communication with the remote light source; and a light guide 1304 having a proximal end in optical communication with an output of the spectral filtering device and one or more distal ends, wherein each distal end is in optical communication with an illumination source (in relation to an external optical imaging device 1301). The elements of the apparatus A correspond to elements as described in relation to FIGS. 1-10.

Still referring to FIG. 13, the optical imaging assembly comprises a working distance greater than approximately 25 cm. The imaging camera comprises an imaging zoom camera. The optical imaging assembly and the imaging zoom camera are configured such that a minimum field of view associated with images collected by the imaging zoom camera is approximately equal to the diameter of a pre-selected access port. The light guide comprises a fiber optic bundle. Each light guide is rotatably attached to a respective illumination source through a rotatable connector. The illumination sources comprise two illumination sources supported on opposite sides of the longitudinal housing. Each illumination source is longitudinally recessed from a distal end of the longitudinal housing. A spacing between the two illumination sources comprises a range of approximately 30 mm to approximately 35 mm. The illumination sources are coupled with the longitudinal housing through a rotatable mounting mechanism. The apparatus A further comprises an attachment mechanism for connecting the longitudinal housing to a robotic positioning arm. The spectral filtering device comprises a dispersive element optically coupled to a spatial light modulator.

Figure 14:
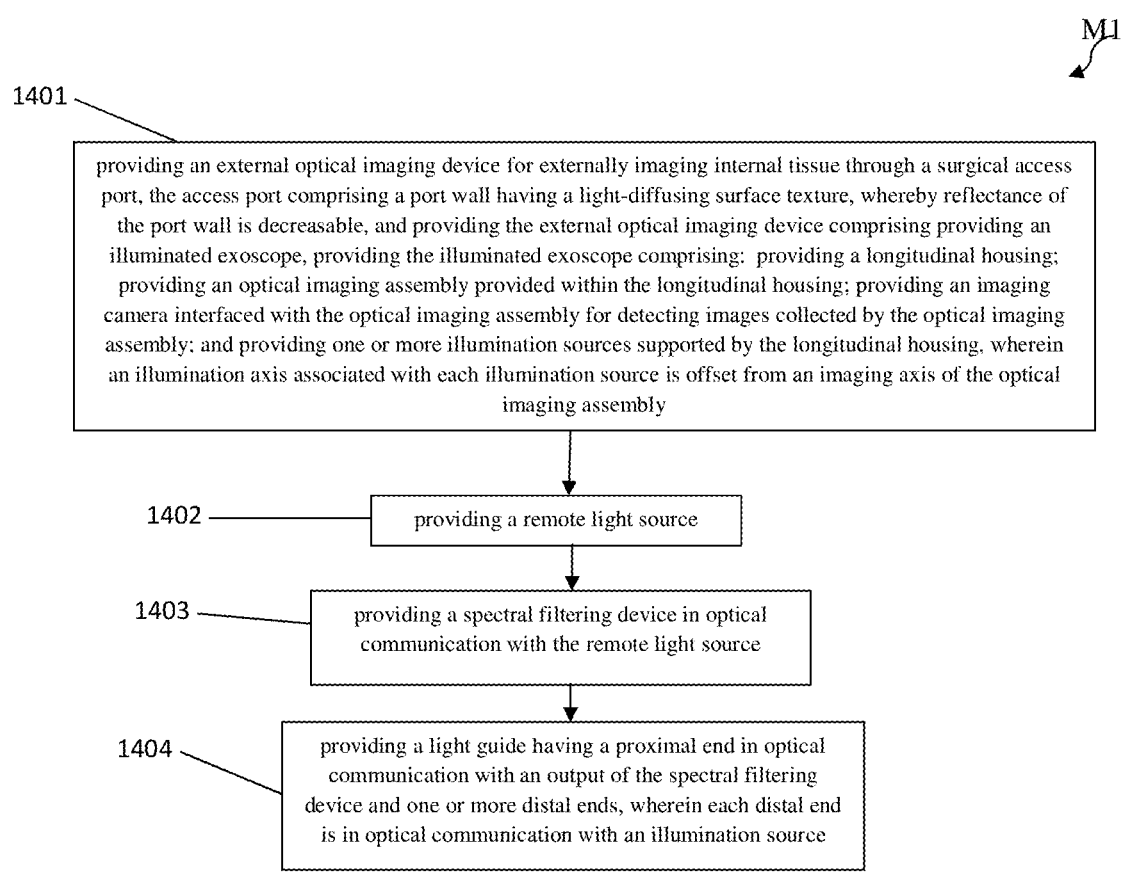
FIG. 14 is a flow diagram illustrating a method of fabricating a method of fabricating a hyperspectral imaging apparatus for performing hyperspectral imaging of a surgical field, in accordance with an embodiment of the present disclosure.

Referring to FIG. 14, this flow diagram illustrates a method M1 of fabricating a hyperspectral imaging apparatus A for performing hyperspectral imaging of a surgical field, in accordance with an embodiment of the present disclosure. The method M1 comprises: providing an external optical imaging device 1301 for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising: providing a longitudinal housing; providing an optical imaging assembly provided within the longitudinal housing; providing an imaging camera interfaced with the optical imaging assembly for detecting images collected by the optical imaging assembly; and providing one or more illumination sources supported by the longitudinal housing, wherein an illumination axis associated with each illumination source is offset from an imaging axis of the optical imaging assembly, as indicated by block 1401; providing a remote light source 1302, as indicated by block 1402; providing a spectral filtering device 1303 in optical communication with the remote light source, as indicated by block 1403; and providing a light guide 1304 having a proximal end in optical communication with an output of the spectral filtering device and one or more distal ends, wherein each distal end is in optical communication with an illumination source, as indicated by block 1404.

Still referring to FIG. 14, in the method M1, providing the optical imaging assembly comprises providing a working distance greater than approximately 25 cm. Providing the imaging camera comprises providing an imaging zoom camera. Providing the optical imaging assembly and providing the imaging zoom camera comprises configuring the optical imaging assembly and the imaging zoom camera such that a minimum field of view associated with images collected by the imaging zoom camera is approximately equal to the diameter of a pre-selected access port. Providing the light guide comprises providing a fiber optic bundle. Providing each light guide comprises providing each light guide as rotatably attached to a respective illumination source through a rotatable connector. Providing the illumination sources comprises providing two illumination sources supported on opposite sides of the longitudinal housing. Providing each illumination source comprises providing each illumination source as longitudinally recessed from a distal end of the longitudinal housing. Providing the two illumination sources comprises providing a spacing between the two illumination sources comprises a range of approximately 30 mm to approximately 35 mm Providing the illumination sources comprises providing the illumination sources as connected to the longitudinal housing through a rotatable mounting mechanism that permits rotation of the illumination sources in an annular path around the longitudinal housing. The method M1 further comprising providing an attachment mechanism for connecting the longitudinal housing to a robotic positioning arm. Providing the spectral filtering device comprises providing a dispersive element optically coupled to a spatial light modulator.

Figure 15:
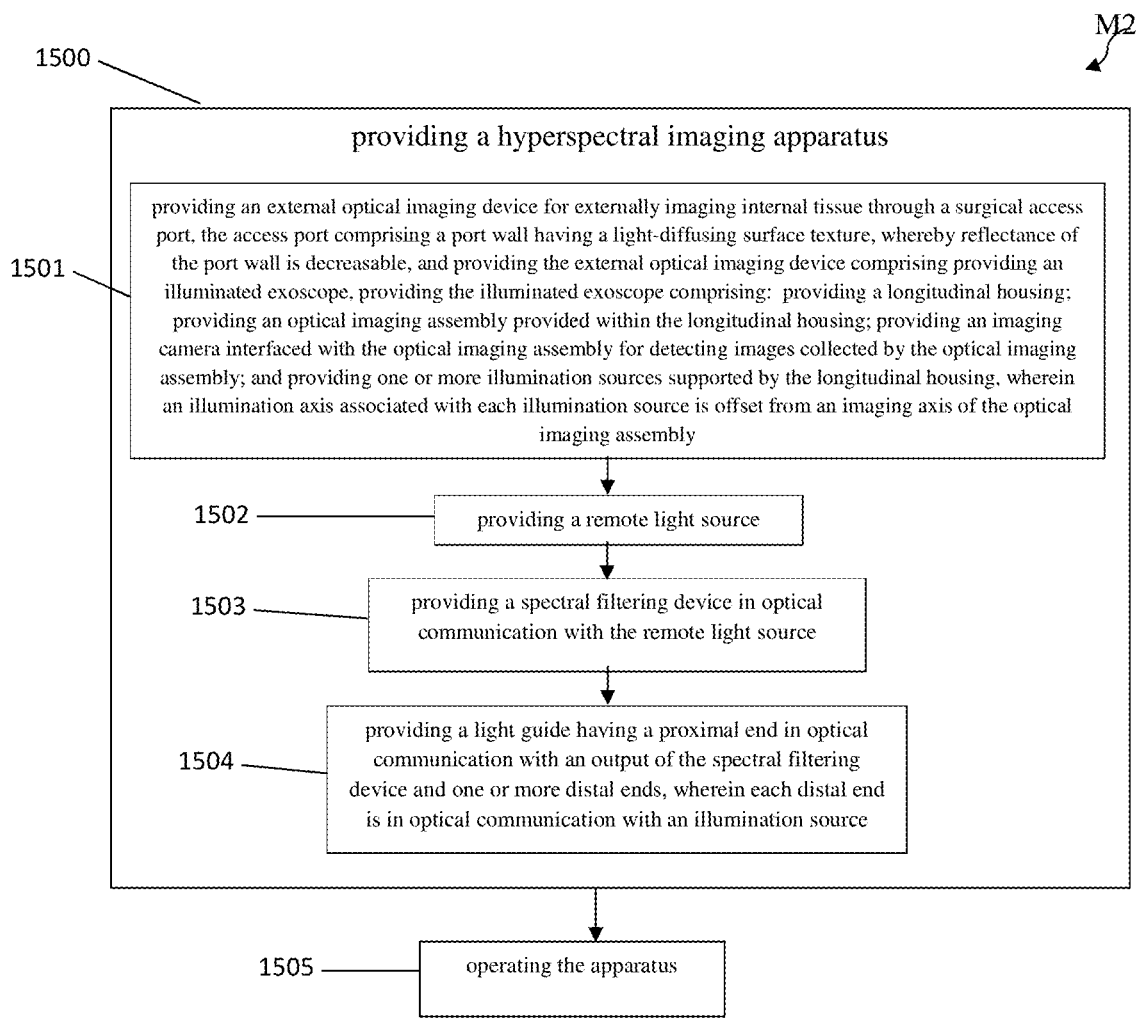
FIG. 15 is a flow diagram illustrating a method a method of performing hyperspectral imaging of a surgical field by way of a hyperspectral imaging apparatus, in accordance with an embodiment of the present disclosure

Referring to FIG. 15, this flow diagram illustrates a method M2 of performing hyperspectral imaging of a surgical field by way of a hyperspectral imaging apparatus A, in accordance with an embodiment of the present disclosure. The method M2 comprises: providing a hyperspectral imaging apparatus A, as indicated by block 1500, providing the apparatus A comprising: providing an external optical imaging device 1301 for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising: providing a longitudinal housing; providing an optical imaging assembly provided within the longitudinal housing; providing an imaging camera interfaced with the optical imaging assembly for detecting images collected by the optical imaging assembly; and providing one or more illumination sources supported by the longitudinal housing, wherein an illumination axis associated with each illumination source is offset from an imaging axis of the optical imaging assembly, as indicated by block 1501; providing a remote light source 1302, as indicated by block 1502; providing a spectral filtering device 1303 in optical communication with the remote light source, as indicated by block 1503; and providing a light guide 1304 having a proximal end in optical communication with an output of the spectral filtering device and one or more distal ends, wherein each distal end is in optical communication with an illumination source, as indicated by block 1504; and operating the apparatus A, as indicated by block 1505.

The specific embodiments described herein are shown, by way of example. Understood is that these embodiments are susceptible to various modifications and alternative forms and that the claims are not intended to be limited to the particular forms disclosed, but rather to cover all modifications, equivalents, and alternatives falling within the spirit and scope of this disclosure. While the Applicant's teachings described herein are in conjunction with various embodiments for illustrative purposes, the Applicant's teachings are not intended as limited to such embodiments. On the contrary, the Applicant's teachings described and illustrated herein encompass various alternatives, modifications, and equivalents, without departing from the embodiments, the general scope of which is defined in the appended claims.

What is claimed:

1. A hyperspectral imaging apparatus for performing hyperspectral imaging of a surgical field, the apparatus comprising:
   an external optical imaging device for externally imaging internal tissue through a surgical access port, the access port comprising a port wall having a light-diffusing surface texture, whereby reflectance of the port wall is decreasable, and the external optical imaging device comprising an illuminated exoscope, the illuminated exoscope comprising:
   a longitudinal housing;
   an optical imaging assembly provided within the longitudinal housing;
   an imaging camera interfaced with the optical imaging assembly for detecting images collected by the optical imaging assembly; and
   one or more illumination sources supported by the longitudinal housing, wherein an illumination axis associated with each illumination source is offset from an imaging axis of the optical imaging assembly;
   a remote light source;
   a spectral filtering device in optical communication with the remote light source; and
   a light guide having a proximal end in optical communication with an output of the spectral filtering device and one or more distal ends, wherein each distal end is in optical communication with an illumination source.

2. The apparatus of claim 1, wherein the optical imaging assembly comprises a working distance greater than approximately 25 cm.

3. The apparatus of claim 1, wherein the imaging camera comprises an imaging zoom camera, and wherein the optical imaging assembly and the imaging zoom camera are configured such that a minimum field of view, associated with images collected by the imaging zoom camera, is approximately equal to a diameter of the access port.

4. The apparatus of claim 1, wherein the light guide comprises a fiber optic bundle.

5. The apparatus of claim 1, wherein each light guide is rotatably coupled with a respective illumination source through a rotatable connector.

6. The apparatus of claim 1, wherein at least one of: the illumination sources comprise two illumination sources supported on opposite sides of the longitudinal housing, and each illumination source is longitudinally recessed from a distal end of the longitudinal housing.

7. The apparatus of claim 6, wherein a spacing between the two illumination sources comprises a range of approximately 30 mm to approximately 35 mm.

8. The apparatus of claim 1, wherein the illumination sources are coupled with the longitudinal housing through a rotatable mounting mechanism that permits rotation of the illumination sources in an annular path around the longitudinal housing.

9. The apparatus of claim 1, further comprising an attachment mechanism for coupling the longitudinal housing with a robotic positioning arm.

10. The apparatus of claim 1, wherein the spectral filtering device comprises a dispersive element optically coupled with a spatial light modulator.

11. A method of fabricating a hyperspectral imaging apparatus for performing hyperspectral imaging of a surgical field, the method comprising:
   providing an external optical imaging device for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising:
   providing a longitudinal housing;
   providing an optical imaging assembly provided within the longitudinal housing;
   providing an imaging camera interfaced with the optical imaging assembly for detecting images collected by the optical imaging assembly; and
   providing one or more illumination sources supported by the longitudinal housing, wherein an illumination axis associated with each illumination source is offset from an imaging axis of the optical imaging assembly;
   providing a remote light source;
   providing a spectral filtering device in optical communication with the remote light source; and
   providing a light guide having a proximal end in optical communication with an output of the spectral filtering device and one or more distal ends, wherein each distal end is in optical communication with an illumination source.

12. The method of claim 11, wherein providing the optical imaging assembly comprises providing a working distance greater than approximately 25 cm.

13. The method of claim 11, wherein providing the imaging camera comprises providing an imaging zoom camera, and wherein providing the optical imaging assembly and providing the imaging zoom camera comprises configuring the optical imaging assembly and the imaging zoom camera such that a minimum field of view associated with images collected by the imaging zoom camera is approximately equal to a diameter of the access port.

14. The method of claim 11, wherein at least one of: providing the light guide comprises providing a fiber optic bundle, and providing each light guide comprises providing each light guide as rotatably coupled with a respective illumination source through a rotatable connector.

15. The method of claim 11, wherein at least one of: providing the illumination sources comprises providing two illumination sources supported on opposite sides of the longitudinal housing, and providing each illumination source comprises providing each illumination source as longitudinally recessed from a distal end of the longitudinal housing.

16. The method of claim 15, wherein providing the two illumination sources comprises providing a spacing between the two illumination sources in a range of approximately 30 mm to approximately 35 mm.

17. The method of claim 11, wherein providing the illumination sources comprises providing the illumination sources as coupled with the longitudinal housing through a rotatable mounting mechanism that permits rotation of the illumination sources in an annular path around the longitudinal housing.

18. The method of claim 11, further comprising providing an attachment mechanism for coupling the longitudinal housing with a robotic positioning arm.

19. The method of claim 11, wherein providing the spectral filtering device comprises providing a dispersive element optically coupled with a spatial light modulator.

20. A method of performing hyperspectral imaging of a surgical field by way of a hyperspectral imaging apparatus, the method comprising:

providing a hyperspectral imaging apparatus, providing the apparatus comprising:

providing an external optical imaging device for externally imaging internal tissue through a surgical access port, the access port comprising a port wall having a light-diffusing surface texture, whereby reflectance of the port wall is decreasable, and providing the external optical imaging device comprising providing an illuminated exoscope, providing the illuminated exoscope comprising:

providing a longitudinal housing;

providing an optical imaging assembly provided within the longitudinal housing;

providing an imaging camera interfaced with the optical imaging assembly for detecting images collected by the optical imaging assembly; and providing one or more illumination sources supported by the longitudinal housing, wherein an illumination axis associated with each illumination source is offset from an imaging axis of the optical imaging assembly;

providing a remote light source;

providing a spectral filtering device in optical communication with the remote light source; and providing a light guide having a proximal end in optical communication with an output of the spectral filtering device and one or more distal ends, wherein each distal end is in optical communication with an illumination source; and operating the apparatus.

\* \* \* \* \*